(12) United States Patent
Lukyanov

(10) Patent No.: US 7,888,113 B2
(45) Date of Patent: Feb. 15, 2011

(54) MODIFIED GREEN FLUORESCENT PROTEINS AND METHODS FOR USING SAME

(75) Inventor: Sergey A. Lukyanov, Moscow (RU)

(73) Assignee: Evrogen Joint Stock Company, Moscow (RU)

( * ) Notice: Subject to any disclaimer, the term of this patent is extended or adjusted under 35 U.S.C. 154(b) by 302 days.

(21) Appl. No.: 12/179,000

(22) Filed: Jul. 24, 2008

(65) Prior Publication Data

US 2009/0117650 A1    May 7, 2009

Related U.S. Application Data

(62) Division of application No. 11/580,348, filed on Oct. 13, 2006, now Pat. No. 7,417,131.

(60) Provisional application No. 60/733,429, filed on Nov. 4, 2005.

(51) Int. Cl.
*C12N 15/00* (2006.01)
*C12N 1/20* (2006.01)
*C07H 21/02* (2006.01)

(52) U.S. Cl. .............. 435/320.1; 536/23.1; 435/252.3

(58) Field of Classification Search ............... 536/23.1; 435/252.3, 320.1
See application file for complete search history.

(56) References Cited

U.S. PATENT DOCUMENTS

| | | |
|---|---|---|
| 5,020,192 A | 6/1991 | Gerlach |
| 5,182,202 A | 1/1993 | Kajiyama et al. |
| 5,221,623 A | 6/1993 | Legocki et al. |
| 5,229,285 A | 7/1993 | Kajiyama et al. |
| 5,330,906 A | 7/1994 | Kajiyama et al. |
| 5,418,155 A | 5/1995 | Cormier et al. |
| 5,439,797 A | 8/1995 | Tsien et al. |
| 5,484,956 A | 1/1996 | Lundquist et al. |
| 5,491,084 A | 2/1996 | Chalfie et al. |
| 5,538,879 A | 7/1996 | Muller-Rober et al. |
| 5,576,198 A | 11/1996 | McBride et al. |
| 5,595,896 A | 1/1997 | Coruzzi et al. |
| 5,618,722 A | 4/1997 | Zenno et al. |
| 5,625,048 A | 4/1997 | Tsien et al. |
| 5,629,470 A | 5/1997 | Lam et al. |
| 5,633,155 A | 5/1997 | Kim et al. |
| 5,650,135 A | 7/1997 | Contag et al. |
| 5,656,466 A | 8/1997 | Moon et al. |
| 5,674,713 A | 10/1997 | McElroy et al. |
| 5,674,731 A | 10/1997 | Lin et al. |
| 5,688,648 A | 11/1997 | Mathies et al. |
| 5,689,045 A | 11/1997 | Logemann et al. |
| 5,689,049 A | 11/1997 | Cigan et al. |
| 5,700,673 A | 12/1997 | McElroy et al. |
| 5,707,804 A | 1/1998 | Mathies et al. |
| 5,728,528 A | 3/1998 | Mathies et al. |
| 5,739,409 A | 4/1998 | Fischer et al. |
| 5,750,870 A | 5/1998 | Mathews et al. |
| 5,767,367 A | 6/1998 | Dudits et al. |
| 5,777,079 A | 7/1998 | Tsien et al. |
| 5,795,737 A | 8/1998 | Seed et al. |
| 5,804,387 A | 9/1998 | Cormack et al. |
| 5,824,485 A | 10/1998 | Thompson et al. |
| 5,843,746 A | 12/1998 | Tatsumi et al. |
| 5,863,727 A | 1/1999 | Lee et al. |
| 5,866,336 A | 2/1999 | Nazarenko et al. |
| 5,869,255 A | 2/1999 | Mathies et al. |
| 5,874,304 A | 2/1999 | Zolotukhin et al. |
| 5,911,952 A | 6/1999 | Tsuji |
| 5,945,283 A | 8/1999 | Kwok et al. |
| 5,945,526 A | 8/1999 | Lee et al. |
| 5,968,738 A | 10/1999 | Anderson et al. |
| 5,968,750 A | 10/1999 | Zolotukhin et al. |
| 5,972,638 A | 10/1999 | Burlage et al. |
| 5,981,200 A | 11/1999 | Tsien et al. |
| 5,989,835 A | 11/1999 | Dunlay et al. |
| 5,998,146 A | 12/1999 | Latva et al. |
| 6,008,373 A | 12/1999 | Waggoner et al. |
| 6,020,192 A | 2/2000 | Muzyczka et al. |
| 6,027,881 A | 2/2000 | Pavlakis et al. |
| 6,046,925 A | 4/2000 | Tsien et al. |
| 6,054,321 A | 4/2000 | Tsien et al. |
| 6,066,476 A | 5/2000 | Tsien et al. |
| 6,077,707 A | 6/2000 | Tsien et al. |
| 6,090,919 A | 7/2000 | Cormack et al. |
| 6,096,865 A | 8/2000 | Michaels |

(Continued)

FOREIGN PATENT DOCUMENTS

WO    WO-0003246    1/2000

OTHER PUBLICATIONS

Communication Pursuant to Article 94(3) EPC issued Jan. 8, 2010 in EP 06 809 023.2.

(Continued)

*Primary Examiner*—Maryam Monshipouri
(74) *Attorney, Agent, or Firm*—Patterson & Sheridan, L.L.P.

(57) ABSTRACT

The present invention provides nucleic acid molecules encoding mutant fluorescent proteins as well as proteins encoded by these nucleic acids. In addition, host-cells, stable cell lines and transgenic organisms comprising the above-referenced nucleic acid molecules are provided. The subject protein and nucleic acid compositions find use in a variety of different applications and methods, particularly for labeling of biomolecules, cells, or cell organelles.

8 Claims, 7 Drawing Sheets

U.S. PATENT DOCUMENTS

| | | |
|---|---|---|
| 6,124,128 A | 9/2000 | Tsien et al. |
| 6,130,313 A | 10/2000 | Li et al. |
| 6,146,826 A | 11/2000 | Chalfie et al. |
| 6,172,188 B1 | 1/2001 | Thastrup et al. |
| 6,194,548 B1 | 2/2001 | Osumi et al. |
| 6,265,548 B1 | 7/2001 | Pavlakis et al. |
| 6,319,669 B1 | 11/2001 | Tsien et al. |
| 6,403,374 B1 | 6/2002 | Tsien et al. |
| 6,414,119 B1 | 7/2002 | Fisher |
| 6,469,154 B1 | 10/2002 | Tsien et al. |
| 6,593,135 B2 | 7/2003 | Wachter et al. |
| 6,638,732 B1 | 10/2003 | Evans |
| 6,699,687 B1 | 3/2004 | Tsien et al. |
| 6,780,975 B2 | 8/2004 | Tsien et al. |
| 6,800,733 B2 | 10/2004 | Tsien et al. |
| 6,803,188 B1 | 10/2004 | Tsien et al. |
| 6,818,443 B2 | 11/2004 | Thastrup et al. |
| 6,852,849 B2 | 2/2005 | Tsien et al. |
| 6,919,186 B2 | 7/2005 | Stubbs et al. |
| 7,417,131 B2 | 8/2008 | Lukyanov |
| 2003/0094868 A1 | 5/2003 | Kronenberg et al. |
| 2003/0170911 A1 | 9/2003 | Tsien et al. |
| 2005/0054050 A1 | 3/2005 | Thastrup et al. |
| 2007/0105196 A1 | 5/2007 | Lukyanov |

OTHER PUBLICATIONS

Response to Communication Pursuant to Article 94(3) EPC issued Jan. 8, 2010 in EP 06 809 023.2 filed Apr. 20, 2010.

Communication Pursuant to Article 94(3) EPC issued Jun. 24, 2010 in EP 06 809 023.2.

MODIFIED GREEN FLUORESCENT PROTEINS AND METHODS FOR USING SAME

CROSS-REFERENCE TO RELATED APPLICATIONS

This application is a divisional of U.S. patent application Ser. No. 11/580,348, filed Oct. 13, 2006, now U.S. Pat. No. 7,417,131 which claims benefit of U.S. provisional patent application Ser. No. 60/733,429, filed Nov. 4, 2005. Each of the aforementioned related patent applications is herein incorporated by reference.

FIELD OF THE INVENTION

This invention relates generally to the field of biology and chemistry. More particularly, the invention is directed to fluorescent proteins.

BACKGROUND OF THE INVENTION

Green Fluorescent Protein (GFP) from the hydromedusa *Aequorea victoria* (synonym A. A.), described by Johnson et al. in J Cell Comp Physiol. (1962), 60:85-104, was found as a part of bioluminescent system of the jellyfish where GFP played the role of a secondary emitter transforming blue light from the photoprotein aequorin into green light.

cDNA encoding *A. victoria* GFP was cloned by Prasher et al. (Gene, 1992, V. 111 (2), pp. 229-233). It turned out that this gene can be heterologously expressed in practically any organism due to unique ability of GFP to form a fluorophore by itself (Chalfie et al., Gene (1992), 111 (2):229-233). This finding opens broad perspectives for use of GFP in cell biology as a genetically encoded fluorescent label.

A great deal of research is being performed to improve the properties of GFP and to produce GFP reagents useful and optimized for a variety of research purposes. New versions of GFP have been developed, such as a "humanized" GFP DNA, the protein product of which has increased synthesis in mammalian cells (Haas, et al., Current Biology 1996, V. 6, pp. 315-324; Yang, et al., Nucleic Acids Research 1996, V. 24, pp. 4592-4593). One such humanized protein is "enhanced green fluorescent protein" (EGFP). Other mutations to GFP have resulted in blue-, cyan- and yellow-green light emitting versions. Also, GFP variants with improved folding and cellular fluorescence under incubation at 37° C. have been obtained. Useful *A. victoria* GFP mutants are described in detail in U.S. Pat. Nos. 5,491,084, 5,625,048, 5,777,079, 5,804,387, 6,090,919, 5,874,304, 5,968,750, 6,020,192, 6,027,881, 6,046,925, 6,054,321, 6,066,476, 6,096,865, 6,146,826, 6,414,119, 6,638,732, 6,699,687, 6,803,188, 6,077,707, 6,124,128, 6,172,188, 6,818,443, 6,194,548, 6,265,548, 6,319,669, 6,403,374, 6,593,135, 6,800,733, 6,780,975, 6,852,849, and 6,919,186.

GFP homologs from different species including Anthozoa and Arthropoda were isolated (Matz et al., Nature Biotechnol. 1999, V. 17, pp. 969-973; Shagin et al., Mol Biol Evol. 2004, V. 21(5), pp. 841-850). A number of biological and biomedical applications of these proteins are discussed in detail by Lippincott-Schwartz and Patterson in Science, 2003, V. 300 (5616), pp. 87-91. Also, close homologues of *A. victoria* GFP were isolated from other jellyfishes the of *Aequorea* genus including *A. macrodactyla* green fluorescent protein, GFPxm (Xia et al., Mar Biotechnol 2002, V. 4(2), pp. 155-62) and *A. coerulescens* GFP-like protein, AcGFPL (Gurskaya et al., Biochem J. (2003), 373(Pt 2): 403-408).

*A. macrodactyla* GFPxm shares 83% identity with *A. victoria* GFP. Wild type GFPxm is not useful as a fluorescent marker in cell-based assays because of a low maturation speed at 37° C. Modification of GFPxm to optimize its maturation speed at temperatures of 35-39° C. provide a means for detecting the reporter in mammalian cells at lower levels of expression and/or increased sensitivity relative to wild type GFPxm. This greatly improves the usefulness of the GFPxm in studying cellular functions in living cells.

SUMMARY OF THE INVENTION

This invention provides functional engineered fluorescent proteins with increased maturation speed at a temperature of 20° C. or above compared to wild type *A. macrodactyla* green fluorescent protein (GFPxm), wherein said functional engineered fluorescent proteins are substantially identical to the amino acid sequence of *A. macrodactyla* green fluorescent protein (GFPxm) (SEQ ID NO:2) and comprise a F220L amino acid substitution.

In a preferred embodiment, the invention provides a nucleic acid molecule comprising a nucleotide sequence encoding a functional fluorescent protein whose amino acid sequence is substantially similar to the amino acid sequence of *A. macrodactyla* green fluorescent protein (GFPxm) (SEQ ID NO:2) and differs from SEQ ID NO:2 by at least an amino acid substitution F220L. Said functional fluorescent protein has an increased maturation speed at a temperature of 20° C. or above as compared with GFPxm.

In a preferred embodiment, a nucleic acid molecule of the present invention encodes a fluorescent protein that also comprises additional amino acid substitutions selected from the group consisting of K3G, E6D, T9A, P58T, F99L, F99H, M128K, M128E, I136M, Y151H, N144S, K162E, K156M, T214A, G228C, G228S, and K238R, wherein said functional fluorescent protein has increased maturation speed at a temperature of 20° C. or above compared to wild-type *A. macrodactyla* GFPxm.

In preferred embodiments, a nucleic acid molecule of the present invention encodes a functional fluorescent protein that is substantially similar to the amino acid sequence of GFPxm and comprises additional one or more amino acid substitution(s) that alter its fluorescent properties and/or optimize folding, as shown for example in SEQ ID NOs: 18-24.

In another preferred embodiment, this invention provides a functional mutant fluorescent protein whose amino acid sequence is substantially similar to the amino acid sequence of *A. macrodactyla* GFPxm (SEQ ID NO:2) and which differs from SEQ ID NO:2 by at least an amino acid substitution F220L. Said functional mutant fluorescent protein has an improved maturation speed at a temperature of 20° C. or above as compared with GFPxm. Examples of mutant fluorescent proteins having amino acid compositions selected from the group consisting of SEQ ID NOS 4-24 are also provided, wherein said mutant fluorescent proteins have an improved maturation speed at a temperature of 20° C. or above as compared with GFPxm.

In yet other embodiments there are provided vectors comprising a nucleic acid of the present invention. In addition, the present invention provides an expression cassette comprising a nucleic acid of the present invention and regulatory elements necessary for expression of the nucleic acid in the cell.

Additionally, host cells, stable cell lines, transgenic animals and transgenic plants comprising nucleic acids, vectors or expression cassettes of the present invention are provided.

DETAILED DESCRIPTION

Figure 1:
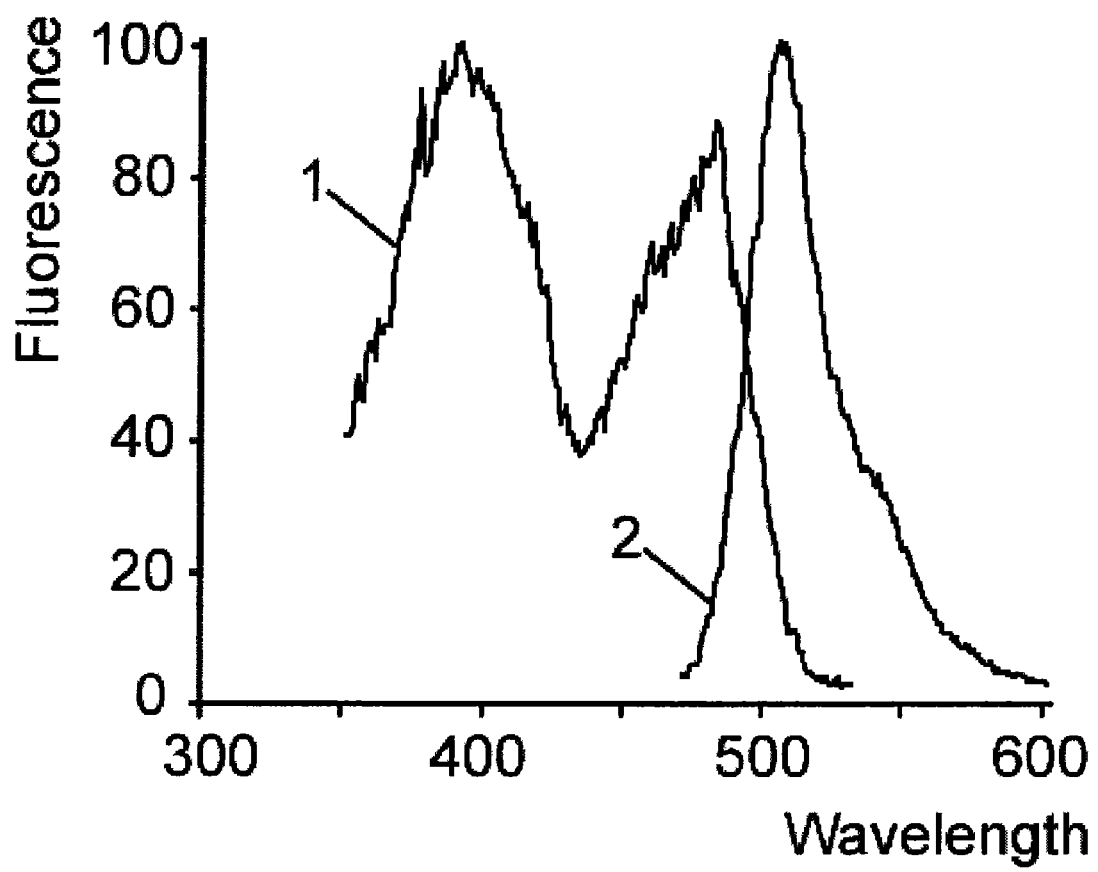
FIG. 1 illustrates the normalized excitation (line 1) and emission (line 2) spectra of GFPxm fluorescent protein.

As used herein the term "fluorescent protein" means a protein that is fluorescent; e.g., it may exhibit low, medium or intense fluorescence upon irradiation with light of the appropriate excitation wavelength. The fluorescent characteristic of fluorescent protein is one that arises from the fluorophore wherein the fluorophore results from autocatalytic cyclization of two or more amino acid residues in the polypeptide backbone. As such, the fluorescent proteins of the present invention do not include proteins that exhibit fluorescence only from residues that act by themselves as intrinsic fluors, i.e., tryptophan, tyrosine and phenylalanine.

As used herein, "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild-type GFPxm and the mutant form is useful. A measurable difference can be determined as the amount of any quantitative fluorescent property, e.g., the amount of fluorescence at a particular wavelength, or the integral of fluorescence over the emission spectrum.

As used herein, "maturation rate" or "maturation speed" refers to the rate of mature fluorescent protein formation (i.e., a fluorescent protein capable of producing fluorescence) after translation. Maturation rate can be characterized with a half-time of maturation. It has been discovered that maturation of fluorescent protein includes two steps: (i) Protein folding that means formation of a protein beta-barrel with a central alpha-helix containing amino acids that will form chromophore. This step is commonly characterized with a rate constant of about $10^{(-2)}s^{(-1)}$ or half-time from several seconds to tens of seconds; (ii) Chromophore maturation, that is protein backbone cyclization and dehydration. This stage is commonly characterized with a rate constant of about $10^{(-4)}s^{(-1)}$ or half-time about several minutes. Therefore, this slower step is the limiting step in green fluorescent protein maturation (Reid B G, Flynn G C. Biochemistry. 1997 V. 36(22), PP. 6786-6791).

As used herein, the term "GFP" refers to the green fluorescent protein from A. victoria, including prior art versions of GFP engineered to provide greater fluorescence or fluoresce in different colors. The sequence of wild type GFP has been disclosed in Prasher et al., Gene 111 (1992), 229-33.

As used herein, the term "GFPxm" refers to the wild type green fluorescent protein from A. macrodactyla.

As used herein the term "isolated" means a molecule or a cell that is an environment different from that in which the molecule or the cell naturally occurs.

Reference to a nucleotide sequence "encoding" a polypeptide means that the sequence, upon transcription and translation of mRNA, produces the polypeptide. This includes both the coding strand, whose nucleotide sequence is identical to mRNA and whose sequence is usually provided in the sequence listing, as well as its complementary strand, which is used as the template for transcription. As any person skilled in the art recognizes, this also includes all degenerate nucleotide sequences encoding the same amino acid sequence. Nucleotide sequences encoding a polypeptide include sequences containing introns.

As used herein the term "mutant" refers to a protein disclosed in the present invention, in which one or more amino acids are added and/or substituted and/or deleted and/or inserted at the N-terminus, and/or the C-terminus, and/or within the native amino acid sequences of the proteins of the present invention. As used herein the term "mutant" refers to a nucleic acid molecule that encodes a mutant protein. Moreover, the term "mutant" refers to any shorter or longer version of the protein or nucleic acid herein.

As used herein, "homologue or homology" is a term used in the art to describe the relatedness of a nucleotide or peptide sequence to another nucleotide or peptide sequence, which is determined by the degree of identity and/or similarity between said sequences compared.

As used herein, an amino acid sequence or a nucleotide sequence is "substantially identical" to a reference sequence if the amino acid sequence or nucleotide sequence has at least 90% sequence identity (e.g. 90%, 93%, 95%, 97%, 98%, 99%, or 100% sequence identity) with the reference sequence over a given comparison window. As used herein, an amino acid sequence or a nucleotide sequence is "substantially similar" to a reference sequence if the amino acid sequence or nucleotide sequence has at least 80% sequence identity (e.g. 80%, 85%, 90%, 95%, 97%, 98%, 99%, or 100% sequence identity) with the reference sequence over a given comparison window. Sequence identity is calculated based on a reference sequence. Algorithms for sequence analysis are known in the art, such as BLAST, described in Altschul et al., J. Mol. Biol., 215, pp. 403-10 (1990).

As summarized above the present invention is directed to nucleic acid molecules comprising nucleotide sequences that encode mutant fluorescent proteins, as well as proteins encoded by these nucleic acids. Proteins of interest are substantially identical to the wild type A. macrodactyla green fluorescent protein GFPxm (SEQ ID NO:2) and comprise at least an amino acid substitution F220L. Said mutants are functional fluorescent proteins having an improved maturation speed at a temperature of 20° C. or above as compared with GFPxm.

In one embodiment, said mutant comprises only a F220L substitution. Inventors of the present invention have discovered that the F220L substitution results in measurable increase of maturation rate of the GFPxm at a temperature of 20° C. or above as compared with wild-type GFPxm. Inventors of the present invention have further discovered that the F220L substitution alters fluorescent properties of the protein as compared with *A. macrodactyla* GFPxm.

In another preferred embodiment, said mutant also comprises additional amino acid substitutions that further increase maturation rate of the protein at a temperature of 20° C. or above, e.g. mutant having amino acid sequence selected from the group consisting of SEQ ID NOS 6, 8, 10, 12, 14, 16, and 18 is provided.

Above-noted mutations in GFPxm may be combined with mutations that further increase folding, reduce oligomerization or influence the spectral properties of GFPxm and its mutants, as shown for example in SEQ ID NOs: 18-24.

In yet other embodiments there are provided vectors comprising a nucleic acid of the present invention. In addition, the present invention provides an expression cassette comprising a nucleic acid of the present invention and regulatory elements necessary for expression of the nucleic acid in the cell.

Also of interest are proteins and nucleic acids that are substantially similar to, or derivatives, or homologues, or mutants of, the above-referenced specific proteins and nucleic acids. In addition, host-cells, stable cell lines and transgenic organisms comprising above-referenced nucleic acid molecules are provided. The subject protein and nucleic acid compositions find use in a variety of different applications and methods, particularly cell and protein labeling applications. Finally, kits for use in such methods and applications are provided.

Nucleic Acid Molecules

The present invention provides nucleic acid molecules comprising nucleotide sequences that encode mutant fluorescent proteins that are substantially identical to the wild type *A. macrodactyla* green fluorescent protein GFPxm (SEQ ID NO:2) and comprise at least an amino acid substitution F220L.

A nucleic acid molecule as used herein is a DNA molecule, such as genomic DNA molecules or cDNA molecules, or an RNA molecule, such as mRNA molecules.

In particular, said nucleic acid molecules are DNA molecules comprising an open reading frame that encodes a fluorescent protein of the invention. The subject nucleic acids are present in an environment other than their natural environment; e.g., they are isolated, present in enriched amounts, or are present or expressed in vitro or in a cell or organism other than their naturally occurring environment. In a preferred embodiment, nucleic acid molecules of the present invention are engineered, i.e. obtained from a naturally occurring protein, e.g. wild type *A. macrodactyla* green fluorescent protein GFPxm, by means of modifications.

The modifications, as well as additions or deletions can be introduced by any method known in the art (see for example Gustin et al., Biotechniques (1993) 14: 22; Barany, Gene (1985) 37: 111-123; and Colicelli et al., Mol. Gen. Genet. (1985) 199:537-539, Sambrook et al., Molecular Cloning: A Laboratory Manual, (1989), CSH Press, pp. 15.3-15.108) including error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-directed mutagenesis, random mutagenesis, gene reassembly, gene site saturated mutagenesis (GSSM), synthetic ligation reassembly (SLR), or a combination thereof. The modifications, additions or deletions may be also introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation or a combination thereof.

Specific nucleic acid molecules of interest comprise nucleotide sequences that encode following fluorescent proteins: Mut 2 (SEQ ID NO 4); Mut 235 (SEQ ID NO 6); Mut 235-1 (SEQ ID NO 8); Mut 235-2 (SEQ ID NO 10); Mut 235-4 (SEQ ID NO 12); Mut-g9 (SEQ ID NO 14); Mut 235-4G6 (SEQ ID NO 16). Also of interest are nucleic acid molecules comprising nucleic acid sequences that encode Mut-g9 mutants, tagGFP (also called macGFP, SEQ ID NO: 18), tagCFP (SEQ ID NO:20), tagYFP1 (SEQ ID NO: 22) and tagYFP2 (SEQ ID NO:24), wherein fluorescent properties of these mutants are altered as compared with Mut-g9 protein.

Examples of nucleotide sequences that encode the foregoing proteins are shown in SEQ ID NOS 3-23.

Each of these particular types of nucleic acid molecules of interest is discussed in greater detail individually in the "Examples" section infra.

Also provided are nucleic acids that hybridize to the above-described nucleic acids under stringent conditions, preferably under high stringency conditions (i.e., complements of the previously-described nucleic acids). An example of stringent conditions is hybridization at 50° C. or higher and 0.1×SSC (15 mM sodium chloride/1.5 mM sodium citrate). Another example of high stringency hybridization conditions is overnight incubation at 42° C. in a solution of 50% formamide, 5×SSC (150 mM NaCl, 15 mM trisodium citrate), 50 mM sodium phosphate (pH7.6), 5×Denhardt's solution, 10% destran sulfate, and 20 µg/ml denatured, sheared salmon sperm DNA, followed by washing in 0.1×SSC at about 65° C. Other high stringency hybridization conditions are known in the art and may also be used to identify nucleic acids of the invention.

In addition, degenerate variants of the nucleic acids that encode the proteins of the present invention are also provided. Degenerate variants of nucleic acids comprise replacements of the codons of the nucleic acid with other codons encoding the same amino acids. In particular, degenerate variants of the nucleic acids are generated to increase its expression in a host cell. In this embodiment, codons of the nucleic acid that are non-preferred or a less preferred in genes in the host cell are replaced with the codons over-represented in coding sequences in genes in the host cell, wherein said replaced codons encode the same amino acid. In a preferred embodiment, nucleic acids of the present invention are humanized. As used herein, the term "humanized" refers to changes made to the nucleic acid sequence to optimize the codons for expression of the protein in mammalian (human) cells (Yang et al., Nucleic Acids Research (1996) 24: 4592-4593). See also U.S. Pat. No. 5,795,737 which describes humanization of proteins.

The nucleic acids of the present invention, the corresponding cDNAs, full-length genes and constructs can be generated synthetically by a number of different protocols known to those of skill in the art. Appropriate nucleic acid constructs are purified using standard recombinant DNA techniques as described in, for example, Sambrook et al., Molecular Cloning: A Laboratory Manual, $2^{nd}$ Ed., (1989) Cold Spring Harbor Press, Cold Spring Harbor, N.Y., and under regulations described in, e.g., United States Dept. of HHS, National Institute of Health (NIH) Guidelines for Recombinant DNA Research.

It has been found that fluorescent proteins can be genetically fused to other target proteins and used as markers to identify the location and amount of the target protein produced. Accordingly, this invention provides nucleic acids encoding fusion proteins that comprise a fluorescent protein and additional amino acid sequences. Such sequences can be, for example, up to about 15, up to about 100, up to about 200 or up to about 1000 amino acids long. The fusion proteins possess the ability to fluoresce that is determined by a fluorescent protein portion.

Also provided are vector and other nucleic acid constructs comprising the subject nucleic acids. Suitable vectors include viral and non-viral vectors, plasmids, cosmids, phages, etc., preferably plasmids, and used for cloning, amplifying, expressing, transferring etc. of the nucleic acid sequence of the present invention in the appropriate host. The choice of appropriate vector is well within the skill of the art, and many such vectors are available commercially. To prepare the constructs, the partial or full-length nucleic acid is inserted into a vector typically by means of DNA ligase attachment to a cleaved restriction enzyme site in the vector. Alternatively, the desired nucleotide sequence can be inserted by homologous recombination in vivo, typically by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems used inter alia for the production of the subject fluorescent proteins or fusion proteins thereof or for replication of the subject nucleic acid molecules. The expression cassette may exist as an extrachromosomal element or may be integrated into the genome of the cell as a result of introduction of said expression cassette into the cell. For expression, the gene product encoded by the nucleic acid of the invention is expressed in any convenient expression system, including, for example, bacterial, yeast, insect, amphibian, or mammalian systems. In the expression vector, a subject nucleic acid is operably linked to a regulatory sequence that can include promoters, enhancers, terminators, operators, repressors and inducers. Methods for preparing expression cassettes or systems capable of expressing the desired product are known for a person skilled in the art.

Cell lines, which stably express the proteins of present invention, can be selected by the methods known in the art (e.g. the co-transfection with a selectable marker such as dhfr, gpt, neomycin, or hygromycin allows the identification and isolation of the transfected cells that contain the gene integrated into a genome).

The above-described expression systems may be used in prokaryotic or eukaryotic hosts. Host-cells such as *E. coli, B. subtilis, S. cerevisiae*, insect cells in combination with baculovirus vectors, or cells of a higher organism such as vertebrates, e.g., COS 7 cells, HEK 293, CHO, *Xenopus oocytes*, etc., may be used for production of the protein.

When any of the above-referenced host cells, or other appropriate host cells or organisms are used to replicate and/or express the nucleic acids of the invention, the resulting replicated nucleic acid, expressed protein or polypeptide is within the scope of the invention as a product of the host cell or organism. The product may be recovered by an appropriate means known in the art.

Proteins

Also provided by the subject invention are functional mutant fluorescent proteins whose amino acid sequences are substantially identical to the amino acid sequence of *A. macrodactyla* GFPxm (SEQ ID NO:2) and which differ from SEQ ID NO:2 by at least an amino acid substitution F220L. Said functional mutant fluorescent proteins have an improved maturation speed at a temperature of 20° C. or above as compare with GFPxm.

In a preferred embodiment, a fluorescent protein of the present invention comprise only a F220L substitution as compared with SEQ ID NO:2 and has increased maturation rate as compared with *A. macrodactyla* GFPxm. In a preferred embodiment, this fluorescent protein also has altered fluorescent properties as compared with *A. macrodactyla* GFPxm.

In another preferred embodiment, the F220L substitution is combined with other mutations to improve the properties of the protein. For example, different combinations of amino acid substitutions selected from the group consisting of K3G, E6D, T9A, P58T, F99L, F99H, M128K, M128E, I136M, Y151H, N144S, K162E, K156M, T214A, G228C, G228S, and K238R further increase protein maturation speed at a temperature of 20° C. or above as shown in the "Example" section.

In many embodiments, the subject proteins have an absorbance maximum ranging from about 300 to 700 nm, usually from about 350 to 650 nm and more usually from about 400 to 600 nm. The subject proteins are fluorescent proteins, by which is meant that they can be excited at one wavelength of light following which they will emit light at another wavelength. The excitation spectra of the subject proteins typically ranges from about 300 to 700 nm. The subject proteins generally have a maximum extinction coefficient that ranges from about 25,000 to 150,000 and usually from about 45,000 to 129,000. The subject proteins typically range in length from about 150 to 300 amino acids and usually from about 200 to 300 amino acid residues, and generally have a molecular weight ranging from about 15 to 35 kDa, usually from about 17.5 to 32.5 kDa.

In certain embodiments, the subject proteins are bright, where by bright is meant that the protein fluorescence can be detected by common methods (e.g., visual screening, spectrophotometry, spectrofluorometry, fluorescent microscopy, by FACS machines, etc.) Fluorescence brightness of particular fluorescent proteins is determined by its quantum yield multiplied by maximal extinction coefficient.

In certain embodiments, the subject proteins has an increased maturation speed at a temperature of 20° C. or above as compared with GFPxm. Maturation speed can be estimated by the time required for proteins to achieve their tertiary structure that gives rise to their fluorescent quality in a certain period of time. In other words, maturation speed of a fluorescent protein can be estimated by fluorescence intensity of host cells expressing subject protein after certain period of time after host cell transfection with an expression construct capable of expressing said fluorescent protein.

In certain embodiments, the subject proteins have an increased maturation speed at a temperature of 20° C. or above, preferably of 30° C. or above, most preferably at a temperature ranging from 35° C. to 39° C., e.g. at 37° C. It is well known that many cells, including mammalian cells, are incubated at approximately 37° C. in order to secure optimal and/or physiologically relevant growth. Cell lines originating from different organisms or tissues may have different relevant temperatures ranging from about 35° C. for fibroblasts to about 38° C.-39° C. for mouse beta-cells.

For example, to compare the maturation speeds of fluorescent proteins at different temperatures, the following approach can be used: host cells (e.g. bacterial cells, preferably *E. coli* cells) are transfected with an expression vector encoding a fluorescent protein under the control of a suitable promoter. In a certain embodiment, fluorescent protein expression starts up immediately after transfection (when a constitutive promoter is used, or due to the leakage of an inducible promoter). In another embodiment, fluorescent protein expression is induced by the method well-known in the art. Host cells and grown on petri dish at 20, 30 or 37° C. for certain periods of time (e.g., 36, 24 and 12 hours after start of fluorescent protein expression) fluorescence of *E. coli* colonies is detected by the common methods (e.g., visual screening, spectrophotometry, spectrofluorometry, fluorescent microscopy, by FACS machines, etc.) and brightness of its fluorescence is calculated.

Specific proteins of interest are mutant green fluorescent proteins: Mut 2 (SEQ ID NO 4); Mut 235 (SEQ ID NO 6); Mut 235-1 (SEQ ID NO 8); Mut 235-2 (SEQ ID NO 10); Mut 235-4 (SEQ ID NO 12); Mut-g9 (SEQ ID NO 14); and Mut 235-4G6 (SEQ ID NO 16). Specific proteins of interest have a maturation speed at a temperature of 20° C. or above higher than GFPxm protein.

Specific proteins of interest are discussed in greater detail individually in the "Examples" section infra.

Proteins that are substantially similar or substantially identical to the specific amino acid sequences of the subject invention, i.e., SEQ ID NOs: 4-16 are also provided. Sequence identity is calculated based on a reference sequence as determined using MegAlign, DNAstar clustal algorithm as described in D. G. Higgins and P. M. Sharp, "Fast and Sensitive multiple Sequence Alignments on a Microcomputer," CABIOS, 5 pp. 151-3 (1989) (using parameters ktuple 1, gap penalty 3, window 5 and diagonals saved 5). In many embodiments, amino acid sequences of interest have much higher sequence identity e.g., 93%, 95%, 97%, 99%, 100%, particularly for the sequence of the amino acids that provide the functional regions of the protein.

Proteins that are mutants of the above-described proteins are also provided. Mutants may retain biological properties of the source proteins, or may have biological properties which differ from the wild type proteins. The term "biological property" of the proteins of the present invention refers to, but is not limited to, fluorescent properties; biochemical properties, such as in vivo and/or in vitro stability (e.g., half-life); maturation speed, aggregation tendency and oligomerization tendency and other such properties. Mutations include single amino acid changes, deletions or insertions of one or more amino acids, N-terminal truncations or extensions, C-terminal truncations or extensions and the like.

Mutants can be generated using standard techniques of molecular biology as described in details in the section "Nucleic acid molecules" above. Mutants described herein includes.

(1) a mutant of the Mut-g9 with enhanced fluorescent properties comprising substitutions I167T, F223S, S65C, and F64L as compared with Mut-g9 (SEQ ID NO:14). Said mutant also possesses increased maturation speed as compared with GFPxm and Mut-9 proteins. The amino acid sequence of this mutant named tagGFP (also macGFP) is shown in SEQ ID NO: 18;

(2) a mutant of the tagGFP with cyan-shift in fluorescence spectra that comprises C65A, Y66W, L99H, I123V, K128E, D129G, F145A, N146I, H148D, V163A, T167I, T203C, T205S, C227Y substitutions as compared with tagGFP. The amino acid sequence of this mutant named tagCFP is shown in SEQ ID NO: 20;

(3) a mutant of the tagGFP with yellow-shift in fluorescence spectra that comprises C65T, I68V, E76K, M153T, F224V, C228S and T203Y substitutions as compared with tagGFP. The amino acid sequence of this mutant named tagYFP is shown in SEQ ID NO: 22.

Given the guidance provided in the Examples, and using standard techniques, those skilled in the art can readily generate a wide variety of additional mutants and test whether a biological (e.g. biochemical, spectral, etc.) property has been altered. For example, fluorescence intensity can be measured using a spectrophotometer at various excitation wavelengths.

The proteins of the present invention are present in the isolated form, by which is meant that the protein is substantially free of other proteins and other naturally-occurring biological molecules, such as oligosaccharides, nucleic acids and fragments thereof, and the like, where the term "substantially free" in this instance means that less than 70%, usually less than 60% and more usually less than 50% of the composition containing the isolated protein is some other natural occurring biological molecule. In certain embodiments, the proteins are present in substantially purified form, where by "substantially purified form" means at least 95%, usually at least 97% and more usually at least 99% pure.

In a preferred embodiment, the subject proteins are synthetically produced, e.g. by expressing a recombinant nucleic acid coding sequence encoding the protein of interest in a suitable host, as described above. Any convenient protein purification procedures may be employed, where suitable protein purification methodologies are described in the Guide to Protein Purification, (Deuthser ed.) (Academic Press, 1990). For example, a lysate may be prepared from the original source and purified using HPLC, exclusion chromatography, gel electrophoresis, affinity chromatography, and the like.

Also provided are fusion proteins comprising a protein of the present invention, or functional fragments thereof, fused, for example, to a degradation sequence, a sequence of subcellular localization (e.g. nuclear localization signal, peroximal targeting signal, Golgi apparatus targeting sequence, mitochondrial targeting sequence, etc.), a signal peptide, or any protein or polypeptide of interest. Fusion proteins may comprise for example, a fluorescent protein of subject invention and a second polypeptide ("the fusion partner") fused in-frame at the N-terminus and/or C-terminus of the fluorescent protein. Fusion partners include, but are not limited to, polypeptides that can bind antibodies specific to the fusion partner (e.g., epitope tags), antibodies or binding fragments thereof, polypeptides that provide a catalytic function or induce a cellular response, ligands or receptors or mimetics thereof, and the like.

Also provided are antibodies that bind specifically to the fluorescent proteins of the present invention. Suitable antibodies may be produced using the techniques known in the art. For example, polyclonal antibodies may be obtained as described in (Harlow and Lane Antibodies: A Laboratory Manual, (1988) Cold Spring Harbor Laboratory Press, Cold Spring Harbor, N.Y.) and monoclonal antibodies may be obtained as described in (Goding Monoclonal Antibodies: Principles and Practice: Production and Application of Monoclonal Antibodies in Cell Biology, Biochemistry and Immunology; 3rd edition, (1996) Academic Press). Chimeric antibodies including humanized antibodies as well as single-chain antibodies and antibody fragments such as Fv, $F(ab')_2$ and Fab are also of interest.

Transgenics

The nucleic acids of the present invention can be used to generate transgenic organisms or site-specific gene modifications in cell lines. Transgenic cells of the subject invention include one or more nucleic acids according to the subject invention present as a transgene. For the purposes of the invention any suitable host cell may be used including prokaryotic (e.g. *Escherichia coli, Streptomyces* sp., *Bacillus subtilis, Lactobacillus acidophilus*, etc) or eukaryotic hostcells. Transgenic organisms of the subject invention can be prokaryotic or eukaryotic organisms including bacteria, cyanobacteria, fungi, plants and animals, in which one or more of the cells of the organism contains heterologous nucleic acid of subject invention introduced by way of human intervention, such as by transgenic techniques well known in the art.

The isolated nucleic acid of the present invention can be introduced into the host by methods known in the art, for example infection, transfection, transformation or transconjugation. Techniques for transferring the nucleic acid molecules (i.e. DNA) into such organisms are widely known and provided in references such as Sambrook et al. (Molecular Cloning: A Laboratory Manual, $3^{nd}$ Ed., (2001) Cold Spring Harbor Press, Cold Spring Harbor, N.Y.).

In one embodiment, the transgenic organism can be a prokaryotic organism. Methods on the transformation of prokaryotic hosts are well documented in the art (for example see Sambrook et al. Molecular Cloning: A Laboratory Manual, 2nd edition (1989) Cold Spring Harbor Laboratory Press and Ausubel et al., Current Protocols in Molecular Biology (1995) John Wiley & Sons, Inc).

In another embodiment, the transgenic organism can be a fungus, for example yeast. Yeast is widely used as a vehicle for heterologous gene expression (for example see Goodey et al., Yeast biotechnology, D R Berry et al, eds, (1987) Allen and Unwin, London, pp 401-429, and King et al., Molecular and Cell Biology of Yeasts, E. F. Walton and G. T. Yarronton, eds, Blackie, Glasgow (1989) pp 107-133). Several types of yeast vectors are available, including integrative vectors, which require recombination with the host genome for their maintenance, and autonomously replicating plasmid vectors.

Another host organism is an animal. Transgenic animals can be obtained by transgenic techniques well known in the art and provided in references such as Pinkert, Transgenic Animal Technology: a Laboratory Handbook, 2nd edition (2203) San Diego: Academic Press; Gersenstein and Vintersten, Manipulating the Mouse Embryo: A Laboratory Manual, 3rd ed, (2002) Nagy A. (Ed), Cold Spring Harbor Laboratory; Blau et al., Laboratory Animal Medicine, 2nd Ed., (2002) Fox J. G., Anderson L. C., Loew F. M., Quimby F. W. (Eds), American Medical Association, American Psychological Association; Gene Targeting: A Practical Approach by Alexandra L. Joyner (Ed.) Oxford University Press; 2nd edition (2000). For example, transgenic animals can be obtained through homologous recombination, where the endogenous locus is altered. Alternatively, a nucleic acid construct is randomly integrated into the genome. Vectors for stable integration include plasmids, retroviruses and other animal viruses, YACs, and the like.

The nucleic acid can be introduced into the cell, directly or indirectly by introduction into a precursor of the cell, by way of deliberate genetic manipulation, such as by microinjection or by infection with a recombinant virus or with a recombinant viral vector and the like. The term genetic manipulation does not include classical cross-breeding, or in vitro fertilization, but rather is directed to the introduction of a recombinant nucleic acid molecule. This nucleic acid molecule may be integrated within a chromosome, or it may be extrachromosomally replicating DNA.

DNA constructs for homologous recombination will comprise at least a portion of a nucleic acid of the present invention, wherein the gene has the desired genetic modification(s), and includes regions of homology to the target locus. DNA constructs for random integration need not include regions of homology to mediate recombination. Conveniently, markers for positive and negative selection may be included. Methods for generating cells having targeted gene modifications through homologous recombination are known in the art, For various techniques for transfecting mammalian cells, see Keown et al., Meth. Enzymol. (1990) 185:527-537.

For embryonic stem (ES) cells, an ES cell line may be employed, or embryonic cells may be obtained freshly from a host, such as a mouse, rat, guinea pig, etc. Such cells are grown on an appropriate fibroblast-feeder layer or grown in the presence of leukemia inhibiting factor (LIF). Transformed ES or embryonic cells may be used to produce transgenic animals using the appropriate technique described in the art.

The transgenic animals may be any non-human animals including non-human mammal (e.g. mouse, rat), a bird or an amphibian, etc., and used in functional studies, drug screening and the like. Representative examples of the use of transgenic animals include those described infra.

Transgenic plants also may be produced. Methods of preparing transgenic plant cells and plants are described in U.S. Pat. Nos. 5,767,367, 5,750,870, 5,739,409, 5,689,049, 5,689,045, 5,674,731, 5,656,466, 5,633,155, 5,629,470, 5,595,896, 5,576,198, 5,538,879, and 5,484,956, the disclosures of which are herein incorporated by reference. Methods of producing transgenic plants also are reviewed in Plant Biochemistry and Molecular Biology (eds. Lea and Leegood, John Wiley & Sons) (1993) pp. 275-295 and in Plant Biotechnology and Transgenic Plants (eds. Oksman-Caldentey and Barz), (2002) 719 p.

For example, embryogenic explants comprising somatic cells may be used for preparation of the transgenic host. Following cell or tissue harvesting, exogenous DNA of interest is introduced into the plant cells, where a variety of different techniques is available for such introduction. With isolated protoplasts, the opportunity arises for introduction via DNA-mediated gene transfer protocols, including incubation of the protoplasts with naked DNA, such as plasmids comprising the exogenous coding sequence of interest in the presence of polyvalent cations (for example, PEG or PLO); or electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, such as auxins and cytokinins.

Other suitable methods for producing plants may be used such as "gene-gun" approach or *Agrobacterium*-mediated transformation available for those skilled in the art.

Methods of Use

The fluorescent proteins of the present invention (as well as other components of the subject invention described above) find use in a variety of different applications. Representative uses for each of these types of proteins will be described below, where the uses described herein are merely exemplary and are in no way meant to limit the use of the proteins of the present invention to those described.

In a preferred embodiment relating to the method for labeling a protein, cell or cell organelle, the subject proteins find use as in vivo labels (or reporter molecules) in cell and molecular biology assays. The assays of interest include but are not limited to assays for gene expression, protein localization and co-localization, protein-protein interactions, protein-nucleic acid interactions, nucleic acid-nucleic acid interactions, cell and cell organelle localization and interactions, etc. The fluorescent proteins of the present invention find use as protein labels, or cell organelle labels in living and fixed cells, as markers in cell or organelle fusion, as a cell or organelle integrity markers, as a transfection markers (e.g. as labels for selection of transfected cells containing an expression vector encoding at least one fluorescent protein of the invention), and as real-time probes working at near physiological concentrations, etc.

For example, the subject proteins find use for identifying and/or measuring the expression of a protein or polypeptide of interest in biological material. This method comprises: i) introducing into a cell a nucleic acid molecule comprising a nucleotide sequence encoding a fluorescent protein according to the present invention wherein said nucleic acid molecule is operatively linked to and under the control of an expression control sequence which controls expression of the protein or polypeptide of interest; ii) expression of said nucleic acid under suitable conditions; and iii) detecting the fluorescence emission of the fluorescent protein as a means of measuring the expression of the protein of interest.

Also, the subject proteins find use for localization of a protein or polypeptide of interest in biological material. This method comprises: i) introducing into a cell a nucleic acid molecule comprising a nucleotide sequence encoding a fluorescent protein according to the present invention wherein said nucleic acid molecule is fused with a sequence encoding a protein or polypeptide of interest and operatively linked to and under the control of an suitable expression control sequence; ii) culturing the cell under conditions suitable for the expression of the protein of interest; and iii) detecting the fluorescence emission of the fluorescent protein as a means of measuring the localization of the protein of interest.

The applications of interest include the use of the subject proteins in fluorescence resonance energy transfer (FRET) methods. In these methods, the subject proteins serve as donor and/or acceptors in combination with a second fluorescent protein or dye, for example, a fluorescent protein as described in Matz et al., Nature Biotechnology 17:969-973 (1999); other fluorescent dyes such as coumarin and its derivatives, 7-amino-4-methylcoumarin and aminocoumarin; bodipy dyes; cascade blue; or fluorescein and its derivatives, such as fluorescein isothiocyanate and Oregon green; rhodamine dyes such as Texas red, tetramethylrhodamine, eosins and erythrosins; cyanine dyes such as Cy3 and Cy5; macrocyclic chealates of lenthaninde ions, such as quantum dye; and chemilumescent dyes such as luciferases, including those described in U.S. Pat. Nos. 5,843,746, 5,700, 673, 5,674,713, 5,618,722, 5,418,155, 5,330,906, 5,229,285, 5,221,623, and 5,182,202, the disclosures of which are herein incorporated by reference.

Specific examples of where FRET assays employing the subject fluorescent proteins include, but are not limited to, those described in: U.S. Pat. Nos. 6,008,373, 5,998,146, 5,981,200, 5,945,526, 5,945,283, 5,911,952, 5,869,255, 5,866,336, 5,863,727, 5,728,528, 5,707,804, 5,688,648, and 5,439,797, the disclosures of which are herein incorporated by reference.

The fluorescent proteins of the present invention find use in a method for detecting the effects of a test substance on the regulation of expression and/or translocation of one or more proteins of interest in a cell. Alternatively, they find use in a method for detecting the expression of a protein of interest and the simultaneous activity of an expression control sequence in response to a test substance. The fluorescent proteins also find use in a method to compare the activity of two or more expression control sequences in a cell in response to a test substance. Such methods may be performed in the presence and in the absence of a test substance whose effect on the process is to be measured.

The fluorescent proteins of the present invention also find use in applications involving the automated screening of arrays of cells expressing fluorescent reporting groups by using microscopic imaging and electronic analysis. Screening can be used for drug discovery and in the field of functional genomics where the subject proteins are used as markers of whole cells to detect changes in multicellular reorganization and migration, for example in the formation of multicellular tubules (blood vessel formation) by endothelial cells, migration of cells through the Fluoroblok Insert system (Becton Dickinson Co.), wound healing, or neurite outgrowth. Screening can also be employed where the proteins of the present invention are used as markers fused to peptides (such as targeting sequences) or proteins that detect changes in intracellular location as an indicator for cellular activity, for example in signal transduction, such as kinase and transcription factor translocation upon stimuli. Examples include protein kinase C, protein kinase A, transcription factor NFkB, and NFAT; cell cycle proteins, such as cyclin A, cyclin B1 and cyclin E; protease cleavage with subsequent movement of the cleaved substrate; phospholipids, with markers for intracellular structures such as the endoplasmic reticulum, Golgi apparatus, mitochondria, peroxisomes, nucleus, nucleoli, plasma membrane, histones, endosomes, lysosomes, or microtubules.

The proteins of the present invention also can be used in high content screening to detect co-localization of other fluorescent fusion proteins with localization markers as indicators of movements of intracellular fluorescent proteins/peptides or as markers alone. Examples of applications involving the automated screening of arrays of cells in which the subject fluorescent proteins find use include U.S. Pat. No. 5,989,835, as well as WO 0017624, WO 00/26408, WO 00/17643, and WO 00/03246, the disclosures of which are herein incorporated by reference.

The fluorescent proteins of the present invention also find use in high throughput screening assays. The subject fluorescent proteins are stable proteins with half-lives of more than 24 hours. Also provided are destabilized versions of the subject fluorescent proteins with decreased half-lives that can be used as transcription reporters for drug discovery. For example, a protein according to the subject invention can be fused with a putative proteolytic signal sequence derived from a protein with shorter half-life, such as a PEST sequence from the mouse ornithine decarboxylase gene, a mouse cyclin B1 destruction box or ubiquitin, etc. For a description of destabilized proteins and vectors that can be employed to produce the same, see e.g., U.S. Pat. No. 6,130,313, the disclosure of which is herein incorporated by reference. Promoters in signal transduction pathways can be detected using destabilized versions of the subject fluorescent proteins for drug screening such as, for example, AP1, NFAT, NFkB, Smad, STAT, p53, E2F, Rb, myc, CRE, ER, GR and TRE, and the like.

The subject proteins can be used as second messenger detectors by fusing the subject proteins to specific domains such as the PKCgamma Ca binding domain, PKCgamma DAG binding domain, SH2 domain or SH3 domain, etc.

Secreted forms of the subject proteins, which in turn can be used in a variety of different applications can be prepared by fusing secreted leading sequences to the subject proteins.

The subject proteins also find use in fluorescence activated cell sorting (FACS) applications. In such applications, the subject fluorescent protein is used as a label to mark a population of cells and the resulting labeled population of cells is then sorted with a fluorescent activated cell sorting device, as is known in the art. FACS methods are described in U.S. Pat. Nos. 5,968,738, and 5,804,387, the disclosures of which are herein incorporated by reference.

The subject proteins also find use as in vivo labels in transgenic animals. For example, expression of the subject protein can be driven by tissue-specific promoters, where such methods find use in research for gene therapy, such as testing efficiency of transgenic expression, among other applications. A representative application of fluorescent proteins in transgenic animals that illustrates such applications is found in WO 00/02997, the disclosure of which is herein incorporated by reference.

Additional applications of the proteins of the present invention include use as markers following injection into cells or animals and in calibration for quantitative measurements, as markers or reporters in oxygen biosensor devices for monitoring cell viability, and as markers or labels for animals, pets, toys, food, and the like.

The subject fluorescent proteins also find use as biosensors in prokaryotic and eukaryotic cells, such as a $Ca^{2+}$ ion indicator, a pH indicator, a phosphorylation indicator, or as an indicator of other ions, such as magnesium, sodium, potassium, chloride and halides. Methods of using fluorescent proteins as biosensors also include those described in U.S. Pat. Nos. 5,972,638, 5,824,485, and 5,650,135 (as well as the references cited therein), the disclosures of which are herein incorporated by reference.

The subject fluorescent proteins also find use as a source of a circularly permuted fluorescent proteins and biosensors thereof. Methods of preparation and use of circularly permuted fluorescent proteins are described in Nagai et al., Proc Natl Acad Sci USA, 2001, V. 98(6), pp. 3197-3202, Nagai et al., Proc Natl Acad Sci USA, 2004, V. 101(29), pp 10554-10559, Filippin et al., J Biol. Chem., 2003, V. 278(40), pp. 39224-34, and U.S. Pat. Nos. 6,469,154 and 6,699,687, the disclosures of which are herein incorporated by reference.

The antibodies of the subject invention, described above, also find use in a number of applications, including the differentiation of the subject proteins from other fluorescent proteins.

Kits

Also provided by the present invention are kits for use in practicing one or more of the above-described applications. In preferred embodiments kits may be used for protein labeling. Kits typically include the protein of the invention as such, or a nucleic acid encoding the same preferably with the elements for expressing the subject proteins, for example, a construct such as a vector comprising a nucleic acid encoding the subject protein. The kit components are typically present in a suitable storage medium, such as a buffered solution, typically in a suitable container. Also present in the kits may be antibodies specific to the provided protein. In certain embodiments, the kit comprises a plurality of different vectors each encoding the subject protein, where the vectors are designed for expression in different environments and/or under different conditions, for example, constitutive expression where the vector includes a strong promoter for expression in mammalian cells or a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit.

The following example is offered by way of illustration and not by way of limitation.

EXAMPLES

Example 1

Generation of Nucleic Acids Encoding Mutant Fluorescent Proteins of GFPxm

A nucleic acid encoding wild-type *A. macrodactyla* GFPxm was synthetically produced. To enhance protein yield in eukaryotic expression systems, GFPxm gene humanization was performed at once. Nucleotide and amino acid compositions for the humanized GFPxm are shown in SEQ ID NOS: 1, 2.

Further random mutagenesis was performed to obtain a library of GFPxm randomly mutated variants using the Diversity PCR Random Mutagenesis kit (CLONTECH), under conditions optimal for 3-4 mutations per 1000 bp. PCR products were cloned into pQE30 vector (Qiagen) and transformed in *E. coli* (XL1-blue strain). *E. coli* colonies expressing mutant proteins were grown at 37° C. and visually screened with a fluorescent stereomicroscope SZX-12 (Olympus) after 12-24 hours of growth.

On the first round, the clone possessing the brightest fluorescence after 18 hours of cell growth was selected. Sequence of the nucleic acid insert from this clone showed that it comprises a F220L substitution as compared with GFPxm protein. Nucleotide and amino acid compositions of this protein named Mut 2 are shown in SEQ ID NOS: 3, 4.

Mut 2 nucleic acid was subjected for the several additional rounds of random mutagenesis resulting in following mutants: (i) second round: Mut 235 (SEQ ID NOS: 5, 6); (ii) third round: Mut 235-1 (SEQ ID NOS: 7, 8); Mut 235-2 (SEQ ID NOS: 9, 10); Mut 235-4 (SEQ ID NOS: 11, 12); (iii) fourth round: Mut-g9 (SEQ ID NOS: 13, 14); Mut 235-4G6 (SEQ ID NOS: 15, 16). According to visual screening data, Mut-g9 mutant comprising amino acid substitutions F220L/K3G/T9A/F99L/M128K/N144S/K162E/T214A/G228C/K238R (comparing with GFPxm) maturates faster at 37° C. than other mutants tested.

Example 2

Characterization of Mutant Fluorescent Proteins

Figure 2:
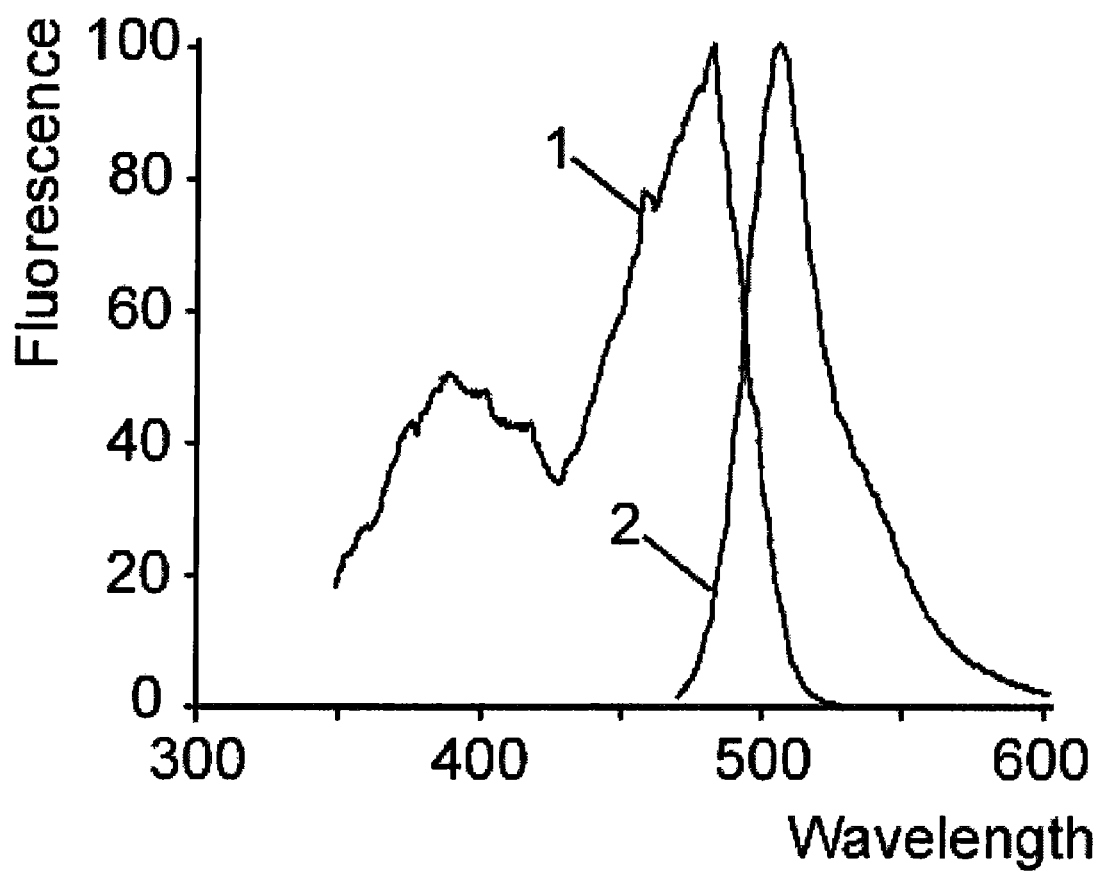
FIG. 2 illustrates the normalized excitation (line 1) and emission (line 2) spectra of Mut 2 fluorescent protein.
Figure 3:
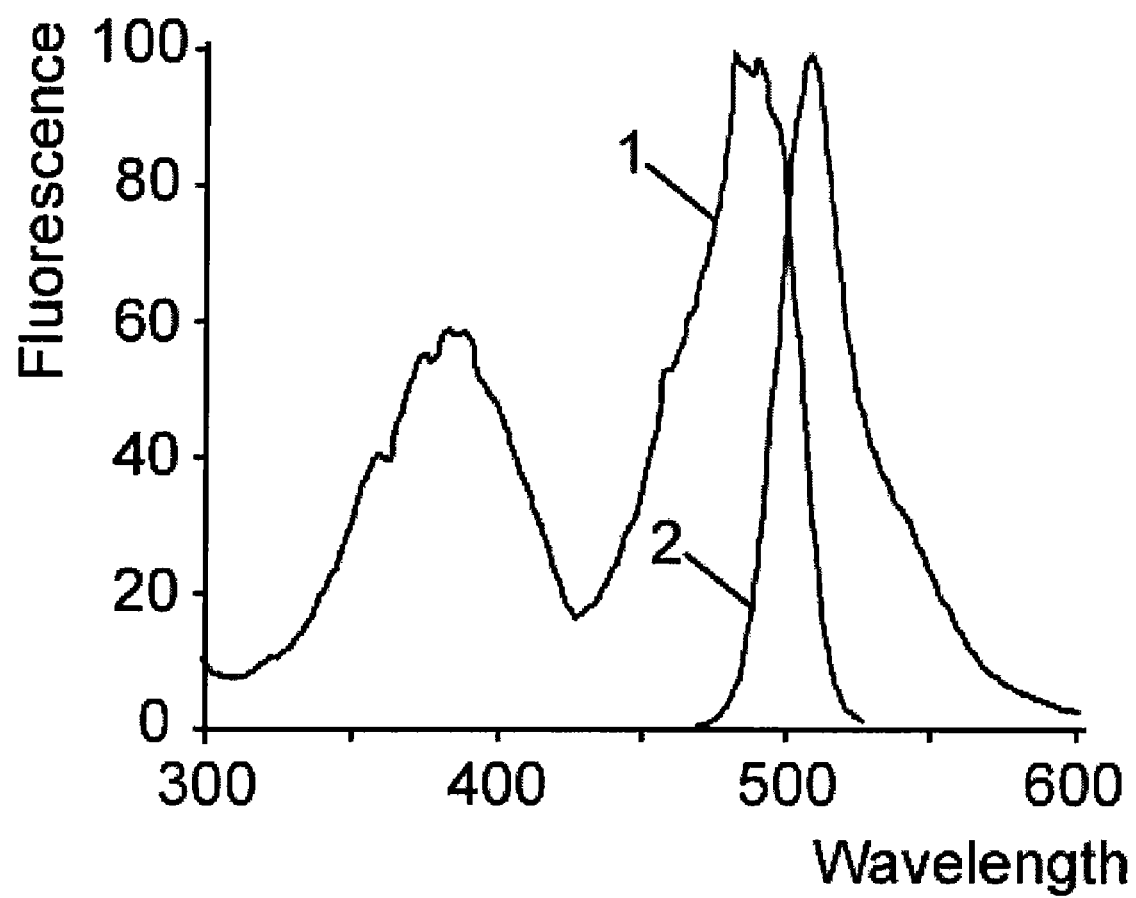
FIG. 3 illustrates the normalized excitation (line 1) and emission (line 2) spectra of Mut-g9 fluorescent protein.

Nucleic acids encoding GFPxm, Mut 2, and Mut-g9 proteins were obtained as described in the Example 1. As described above, these nucleic acids were cloned into a pQE30 expressing vector (Qiagen), so that recombinant protein contained a six-histidine tag at its N-terminus. After expression in *E. coli*, the proteins were purified via a metal-affinity resin TALON (Clontech). Excitation-emission spectra were obtained using Varian Cary Eclipse Fluorescence Spectrophotometer. Excitation-emission spectra for these proteins are shown in FIGS. 1-3. It was shown that the F220L mutation alters fluorescent properties of the fluorescent protein.

Maturation rates of these proteins were characterized in two in vivo systems. In the first experiment, *E. coli* (XL1-blue strain) cells were transformed with pQE30 (Qiagen) encoding the corresponding fluorescent proteins under the control of T5 promoter and grown on a petri dish at 20, 30 or 37° C. for 36, 24 and 12 hours respectively. In the system used, fluorescent protein is constantly expressed and maturated during *E. coli* growth due to the promoter leakage. After cell growth under conditions mentioned, the fluorescent colonies were photographed using an Olympus US SZX12 fluorescent stereo microscope completed with an Olympus DP50 camera. Brightness of the colonies was calculated using ImageJ software. Measuring results are shown in a histogram in FIG. 4.

Figure 5:
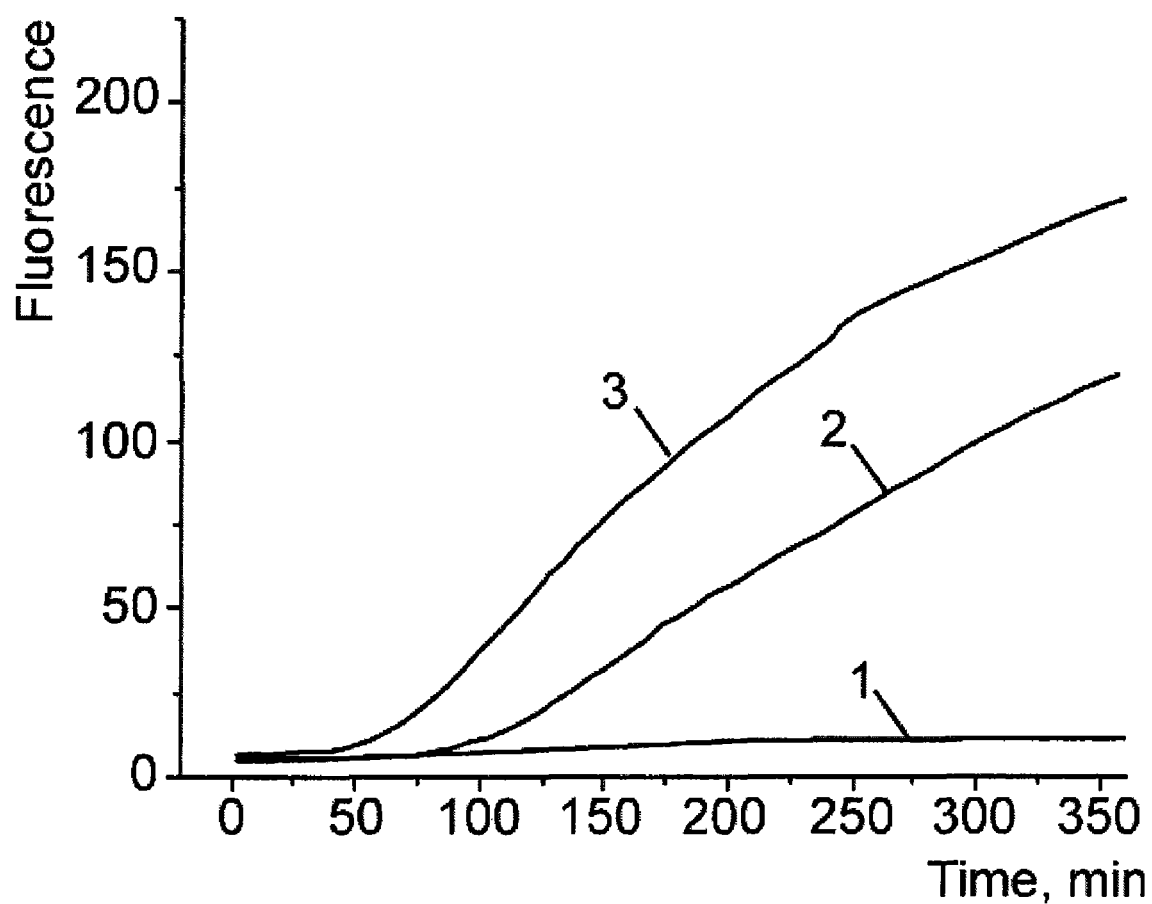
FIG. 5 shows curves of fluorescence growth of E. coli colonies expressing GFPxm (line 1), Mut 2 (line 2), or Mut-g9 (line 3) during 6 hours after induction.

In the another experiment, individual *E. coli* colonies carrying fluorescent protein encoding vectors were grown in LB medium supplemented with 2% glucose and 100 µg/ml ampicillin for 5 hours, centrifuged and placed in the Tris HCl buffer, pH 7.5 containing 100 mM NaCl. Intense fluorescent protein expression was induced at 37° C. by addition of IPTG to 1 mM final concentration. Growth of the fluorescence signal at 37° C. due to the expression and maturation of synthesized fluorescent protein was monitored using a Varian Cary Eclipse Fluorescence Spectrophotometer in Kinetics software for 6 hours (FIG. 5).

Figure 4:
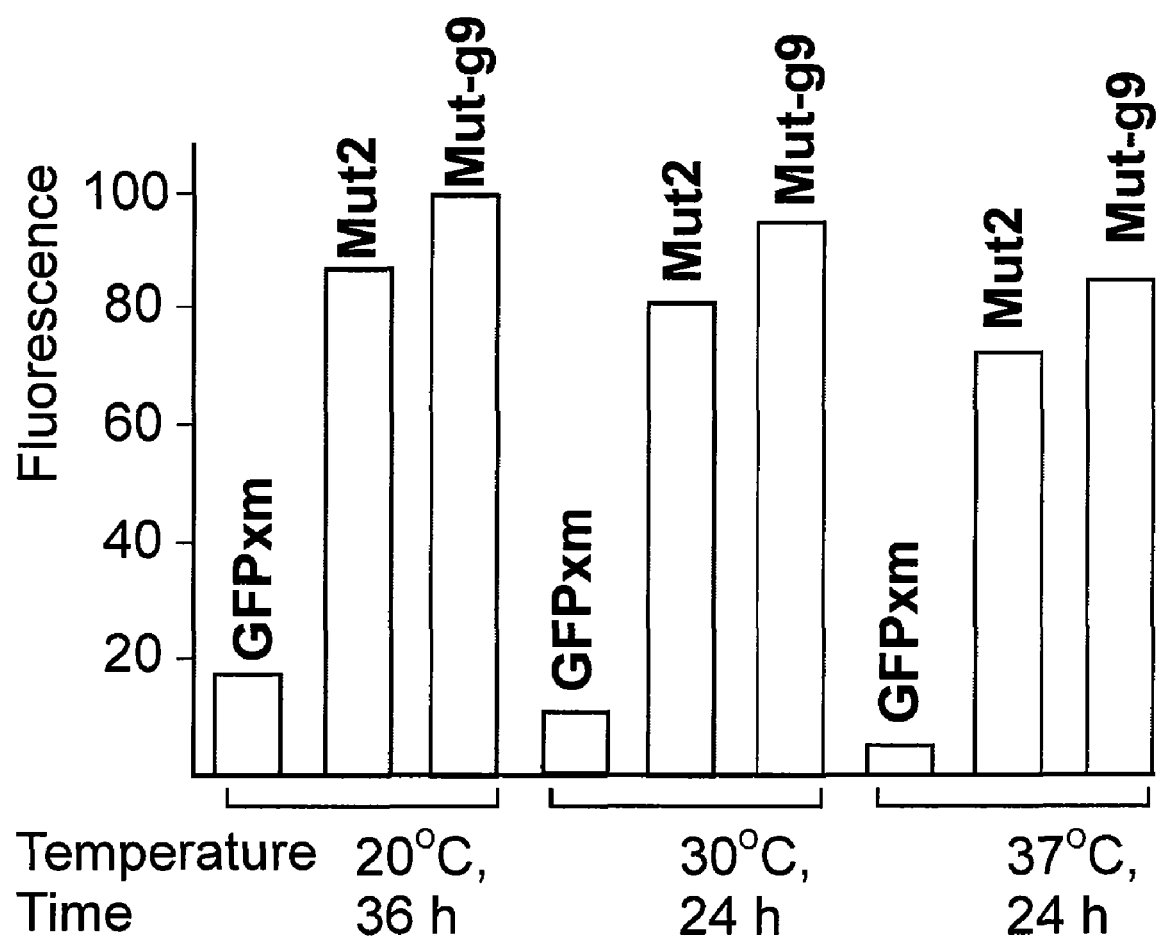
FIG. 4 shows the relative brightness of E. coli colonies expressing GFPxm, Mut 2, or Mut-g9 fluorescent protein after growth at different temperatures. Temperature conditions and incubation time are indicated at the bottom of histogram. All data are normalized to the brightness of Mut-g9 expressing colonies after 36 hours growth at 20° C.

In both experimental systems, maturation rate of the proteins increases in the order shown: GFPxm<Mut 2<Mut-g9 (FIGS. 4, 5).

Example 3

Mut-g9 Mutagenesis

Figure 6:
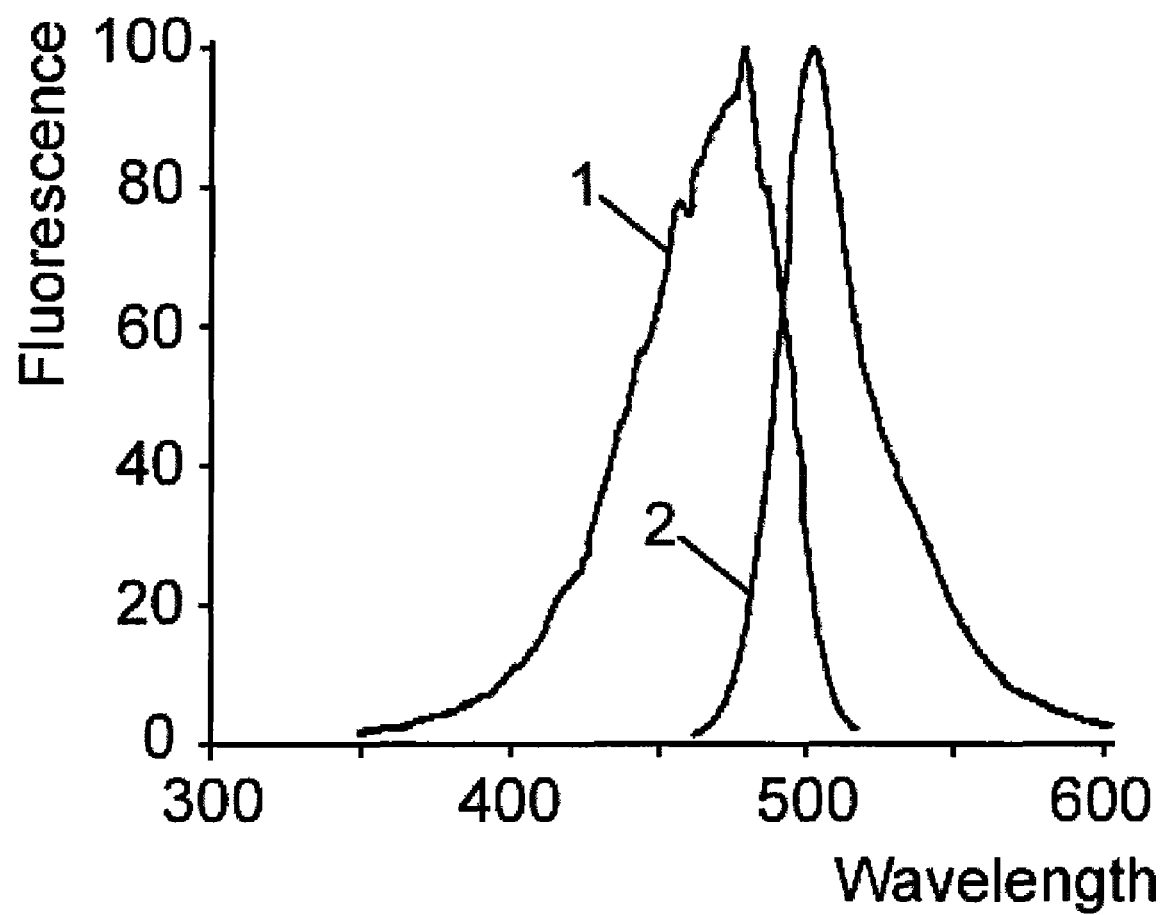
FIG. 6 illustrates the normalized excitation (line 1) and emission (line 2) spectra of tagGFP.

Nucleic acid encoding Mut-g9 protein was obtained as described in the Example 1 and subjected to site directed mutagenesis to obtain variants with altered fluorescent properties and depressed capacity to form dimers. As a result, tagGFP protein (SEQ ID NOS: 17, 18) was obtained containing the following amino acid substitutions (as compared with Mut-g9): I167T, F223S, S65C, F64L. Excitation-emission spectra for this protein are shown at FIG. 6. The maturation rate of this protein was higher than that of GFPxm Mut-2 and Mut-g9 proteins. The maturation rate was tested as described in the Example 2.

Additionally, tagGFP variants with altered spectra of fluorescence were produced by site directed mutagenesis of T203 and Y66 positions resulted in a yellow-shifted variant (excitation/emission peaked at 502/521 nm) comprising T203Y and F224V substitutions, and a cyan-shifted variant (excitation/emission peaked at 430/470 nm) comprising a Y66W substitution. Nucleic acids encoding these spectral variants were used for random mutagenesis to improve protein folding (as shown upon expression in *E. coli*, strain XL1-Blue). These resulted in the cyan fluorescent protein tagCFP with nucleotide and amino acid sequences shown in SEQ ID NOS: 19, 20 and the yellow fluorescent protein tagYFP1 with nucleotide and amino acid sequences shown in SEQ ID NOS: 21, 22.

Figure 7A:
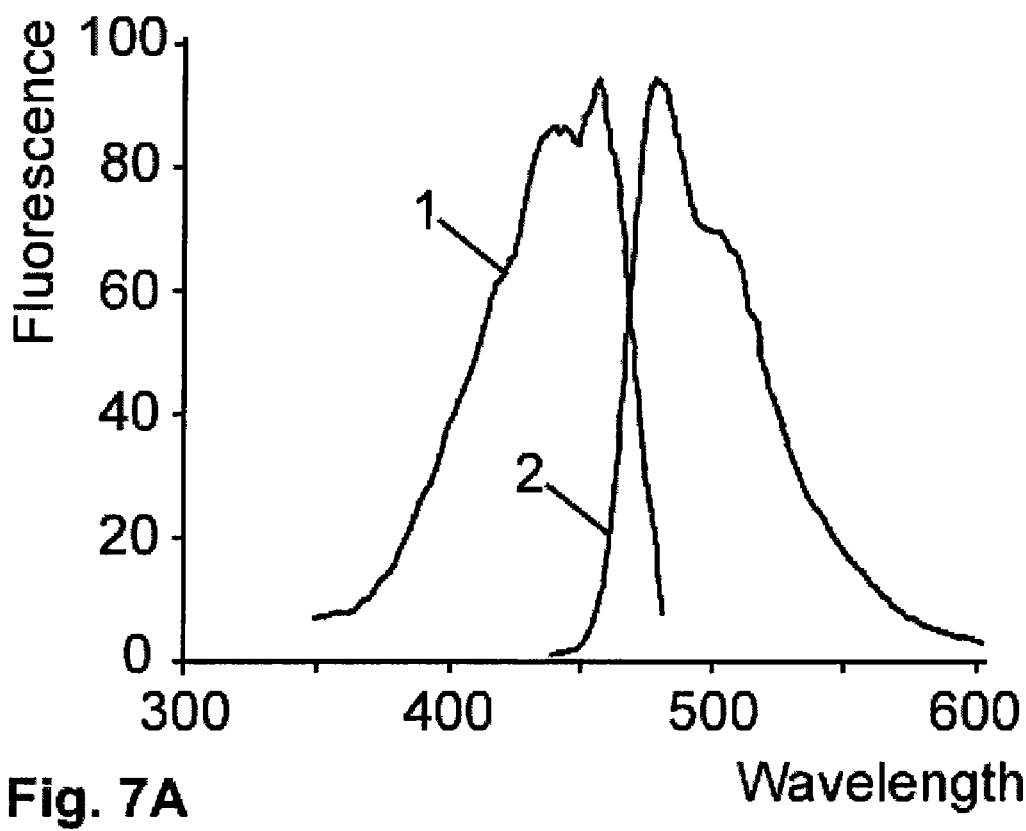
FIG. 7A illustrates the normalized excitation (line 1) and emission (line 2) spectra of tagCFP.
Figure 7B:
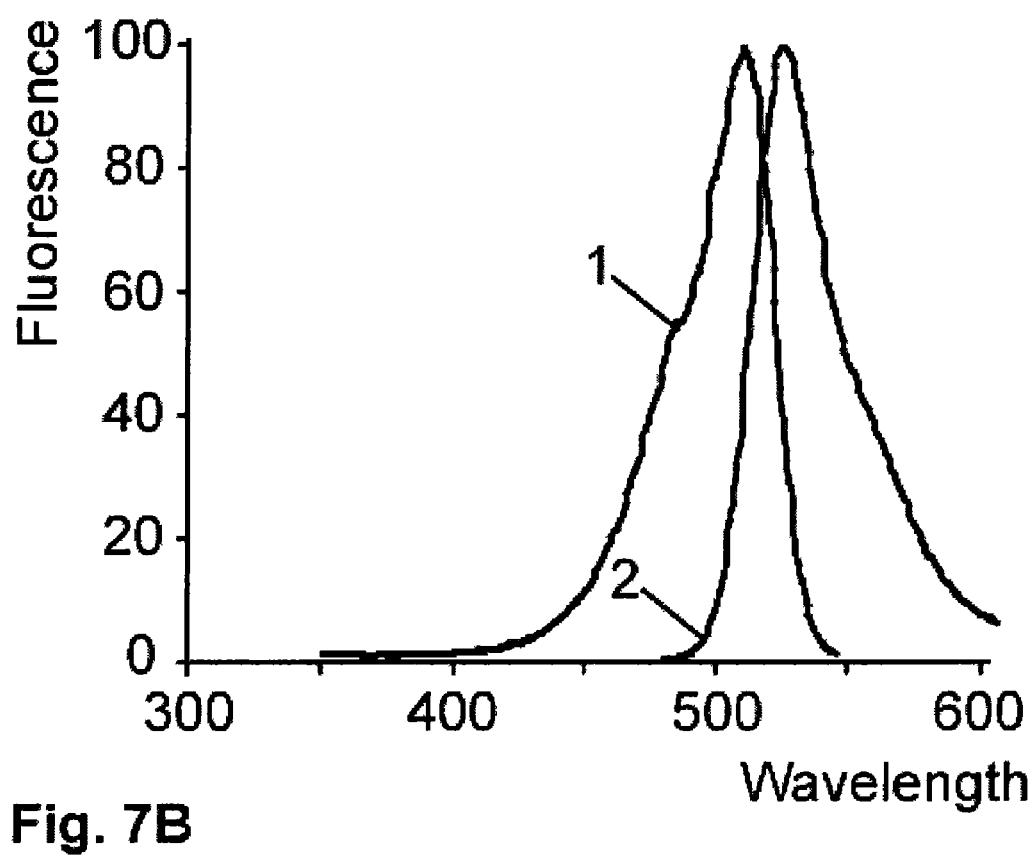
FIG. 7B illustrates the normalized excitation (line 1) and emission (line 2) spectra of tagYFP1.

As compared with tagGFP, tagCFP comprises a Y66W substitution in combination with C65A, L99H, I123V, K128E, D129G, F145A, N146I, H148D, V163A, T167I, T203C, T205S, and C227Y, while tagYFP1 comprises T203Y, F224V substitutions in combination with C65T, 168V, E76K, M153T, and C228S substitutions. Excitation-emission spectra for these proteins are shown in FIGS. 7A and 7B.

An addition, a mutant of tagYFP with a reduced oligomerization tendency, named tagYFP2 (SEQ IDs:23, 24), was also generated by site-directed mutagenesis of the A206 residue. This protein exists as monomer even at high (5 mg/ml) concentrations, as has been shown by gel-filtration.

Example 4

Mammalian Cell Labeling using tagGFP, tagCFP and taqYFP1

For fluorescent labelling of eukaryotic cells, nucleic acids encoding tagGFP, tagCFP and tagYFP1 prepared as described above in the Example 3 were separately cloned into pEGFP-C1 vector (CLONTECH) between AgeI and BglII restriction sites (in lieu of the EGFP-coding region). The following cell lines were used: 293T human kidney epithelial cells, 3T3 mouse embryo fibroblasts, L929 murine subcutaneous fibroblasts, Vero African green monkey kidney epithelial cells and COS1 African green monkey kidney fibroblasts. Cells were transfected using LipofectAMINE reagent (Invitrogen) and were tested 20 h after transfection. An Olympus CK40 fluorescence microscope equipped with a CCD camera (DP-50, Olympus) was used for cell imaging. Expression of these proteins in different cell lines resulted in bright fluorescent signals without aggregation. Fluorescence was clearly detectable within 24 hours after transfection. No cell toxicity was observed.

Example 5

Protein and Organelle Labeling using tagGFP and tagCFP

Nucleic acids encoding tagGFP and tagCFP prepared as described above in the Example 3 were operatively linked with a nucleic acids encoding either human cytoplasmic beta-actin, alpha-tubulin, fibrillarin, or mitochondria-targeted sequence from subunit VIII precursor of human cytochrome C oxidase. Transfection of 293T and HeLa human cells with the above-noted plasmids expressing fusions of fluorescent proteins with host cellular proteins and/or localization signals resulted in bright fluorescence that revealed patterns closely agreeing to that observed for fusions with EGFP.

All publications and patent applications cited in this specification are incorporated by reference herein as if each individual publication or patent application were specifically and individually indicated to be incorporated by reference. The citation of any publication is to provide context and understanding of the present invention and should not be construed as an admission that any such publication is prior art.

What is claimed is:

1. An isolated nucleic acid, comprising a nucleic acid sequence encoding a genetically engineered fluorescent protein that has at least 95% identity with the amino acid sequence of SEQ ID NO: 22.

2. An isolated nucleic acid of claim 1, wherein the genetically engineered fluorescent protein has at least 97% identity with the amino acid sequence of SEQ ID NO: 22.

3. The nucleic acid of claim 1, wherein the genetically engineered fluorescent protein has the amino acid sequence of SEQ ID NO: 22.

4. A vector comprising the nucleic acid of claim 1.

5. An expression cassette comprising:
   (a) a transcriptional initiation region that is functional in an expression host;
   (b) the nucleic acid according to claim 1; and
   (c) and a transcriptional termination region functional in said expression host.

6. An host cell or progeny thereof, comprising the expression cassette according to claim 5 as part of an extrachromosomal element or integrated into the genome of a host cell as a result of introduction of said expression cassette into said host cell.

7. A transgenic cell, or progeny thereof, comprising the nucleic acid according to claim 1.

8. A kit comprising at least one nucleic acid according to claim 1.

* * * * *

SEQUENCE LISTING

<160> NUMBER OF SEQ ID NOS: 24

<210> SEQ ID NO 1
<211> LENGTH: 717
<212> TYPE: DNA
<213> ORGANISM: Artificial sequence
<220> FEATURE:
<223> OTHER INFORMATION: Nucleotide sequence with humanized codon
      usage encoding Aequorea macrodactyla GFPxm green fluorescent
      protein

<400> SEQUENCE: 1

```
atgagcaagg gcgaggagct gttcaccggc atcgtgcccg tgctgatcga gctggacggc    60
gacgtgcacg gccacaagtt cagcgtgcgc ggcgagggcg agggcgacgc cgactacggc   120
aagctggaga tcaagttcat ctgcaccacc ggcaagctgc ccgtgccctg gcccaccctg   180
gtgaccacct tcagctacgg catccagtgc ttcgcccgct accccgagca catgaagatg   240
aacgacttct tcaagagcgc catgcccgag ggctacatcc aggagcgcac catcttcttc   300
caggacgacg gcaagtacaa gacccgcggc gaggtgaagt tcgagggcga caccctggtg   360
aaccgcatcg agctgaaggg catggacttc aaggaggacg gcaacatcct gggccacaag   420
ctggagtaca acttcaacag ccacaacgtg tacatcatgc ccgacaaggc caacaacggc   480
ctgaaggtga acttcaagat ccgccacaac atcgagggcg gcggcgtgca gctggccgac   540
cactaccaga ccaacgtgcc cctgggcgac ggccccgtgc tgatccccat caaccactac   600
ctgagcaccc agaccgccat cagcaaggac cgcaacgaga cccgcgacca catggtgttc   660
ctggagttct tcagcgcctg cggccacacc cacggcatgg acgagctgta caagtga      717
```

<210> SEQ ID NO 2
<211> LENGTH: 238
<212> TYPE: PRT
<213> ORGANISM: Aequorea macrodactyla

<400> SEQUENCE: 2

```
Met Ser Lys Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Phe
    50                  55                  60

Ser Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Met Pro Asp Lys Ala Asn Asn Gly
145                 150                 155                 160

Leu Lys Val Asn Phe Lys Ile Arg His Asn Ile Glu Gly Gly Gly Val
```

```
                    165                 170                 175
Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Ala Ile Ser
        195                 200                 205

Lys Asp Arg Asn Glu Thr Arg Asp His Met Val Phe Leu Glu Phe Phe
    210                 215                 220

Ser Ala Cys Gly His Thr His Gly Met Asp Glu Leu Tyr Lys
225                 230                 235

<210> SEQ ID NO 3
<211> LENGTH: 717
<212> TYPE: DNA
<213> ORGANISM: Artificial sequence
<220> FEATURE:
<223> OTHER INFORMATION: Mut 2 of Aequorea macrodactyla GFPxm
      protein, nucleotide sequence with humanized codon usage

<400> SEQUENCE: 3
atgagcaagg gcgaggagct gttcaccggc atcgtgcccg tgctgatcga gctggacggc    60
gacgtgcacg gccacaagtt cagcgtgcgc ggcgagggcg agggcgacgc cgactacggc   120
aagctggaga tcaagttcat ctgcaccacc ggcaagctgc ccgtgccctg gcccaccctg   180
gtgaccacct tcagctacgg catccagtgc ttcgcccgct accccgagca catgaagatg   240
aacgacttct tcaagagcgc catgcccgag ggctacatcc aggagcgcac catcttcttc   300
caggacgacg gcaagtacaa gacccgcggc gaggtgaagt cgagggcga cacccctggtg   360 aaccgcatcg agctgaaggg catggacttc aaggaggacg gcaacatcct gggccacaag   420
ctggagtaca acttcaacag ccacaacgtg tacatcatgc cgacaaggc caacaacggc    480 ctgaaggtga acttcaagat ccgccacaac atcgagggcg cggcgtgca gctggccgac   540 cactaccaga ccaacgtgcc cctgggcgac ggccccgtgc tgatccccat caaccactac   600
ctgagcaccc agaccgccat cagcaaggac cgcaacgaga cccgcgacca catggtgctc   660
ctggagttct tcagcgcctg cggccacacc cacggcatgg acgagctgta caagtga      717

<210> SEQ ID NO 4
<211> LENGTH: 238
<212> TYPE: PRT
<213> ORGANISM: Artificial sequence
<220> FEATURE:
<223> OTHER INFORMATION: Mut 2 protein derived from Aequorea
      macrodactyla GFPxm

<400> SEQUENCE: 4

Met Ser Lys Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Phe
    50                  55                  60

Ser Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
```

```
                100                 105                 110
Lys Phe Glu Gly Asp Thr Leu Val Asn Arg Ile Glu Leu Lys Gly Met
            115                 120                 125

Asp Phe Lys Glu Asp Gly Asn Ile Leu Gly His Lys Leu Glu Tyr Asn
        130                 135                 140

Phe Asn Ser His Asn Val Tyr Ile Met Pro Asp Lys Ala Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Ala Ile Ser
                195                 200                 205

Lys Asp Arg Asn Glu Thr Arg Asp His Met Val Leu Leu Glu Phe Phe
        210                 215                 220

Ser Ala Cys Gly His Thr His Gly Met Asp Glu Leu Tyr Lys
225                 230                 235
```

<210> SEQ ID NO 5
<211> LENGTH: 717
<212> TYPE: DNA
<213> ORGANISM: Artificial sequence
<220> FEATURE:
<223> OTHER INFORMATION: Mut 235 protein derived from Aequorea
      macrodactyla GFPxm, nucleotide sequence with humanized codon
      usage

<400> SEQUENCE: 5

```
atgagcgggg gcgaggagct gttcaccggc atcgtgcccg tgctgatcga gctggacggc    60
gacgtgcacg gccacaagtt cagcgtgcgc ggcgagggcg agggcgacgc cgactacggc   120
aagctggaga tcaagttcat ctgcaccacc ggcaagctgc ccgtgccctg gcccaccctg   180
gtgaccacct tcagctacgg catccagtgc ttcgcccgct accccgagca catgaagatg   240
aacgacttct tcaagagcgc catgcccgag ggctacatcc aggagcgcac catcttcttc   300
caggacgacg gcaagtacaa gacccgcggc gaggtgaagt tcgagggcga caccctggtg   360
aaccgcatcg agctgaaggg catggacttc aaggaggacg gcaacatcct gggccacaag   420
ctggagtaca gcttcaacag ccacaacgtg tacatcatgc ccgacaaggc caacaacggc   480
ctgaaggtga acttcaagat ccgccacaac atcgagggcg gcggcgtgca gctggccgac   540
cactaccaga ccaacgtgcc cctgggcgac ggccccgtgc tgatccccat caaccactac   600
ctgagcaccc agaccgccat cagcaaggac cgcaacgagg cccgcgacca catggtgctc   660
ctggagttct cagcgcctg cggccacacc cacggcatgg acgagctgta caggtga      717
```

<210> SEQ ID NO 6
<211> LENGTH: 238
<212> TYPE: PRT
<213> ORGANISM: Artificial sequence
<220> FEATURE:
<223> OTHER INFORMATION: Mut 235 protein derived from Aequorea
      macrodactyla GFPxm

<400> SEQUENCE: 6

```
Met Ser Gly Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30
```

-continued

Gly Glu Gly Asp Ala Asp Tyr Gly Lys Leu Glu Ile Lys Phe Ile Cys
    35                  40                  45
Thr Thr Gly Lys Leu Pro Val Pro Trp Pro Thr Leu Val Thr Thr Phe
50                  55                  60
Ser Tyr Gly Ile Gln Cys Phe Ala Arg Tyr Pro Glu His Met Lys Met
65                  70                  75                  80
Asn Asp Phe Phe Lys Ser Ala Met Pro Glu Gly Tyr Ile Gln Glu Arg
                85                  90                  95
Thr Ile Phe Phe Gln Asp Asp Gly Lys Tyr Lys Thr Arg Gly Glu Val
            100                 105                 110
Lys Phe Glu Gly Asp Thr Leu Val Asn Arg Ile Glu Leu Lys Gly Met
        115                 120                 125
Asp Phe Lys Glu Asp Gly Asn Ile Leu Gly His Lys Leu Glu Tyr Ser
    130                 135                 140
Phe Asn Ser His Asn Val Tyr Ile Met Pro Asp Lys Ala Asn Asn Gly
145                 150                 155                 160
Leu Lys Val Asn Phe Lys Ile Arg His Asn Ile Glu Gly Gly Gly Val
                165                 170                 175
Gln Leu Ala Asp His Tyr Gln Thr Asn Val Pro Leu Gly Asp Gly Pro
            180                 185                 190
Val Leu Ile Pro Ile Asn His Tyr Leu Ser Thr Gln Thr Ala Ile Ser
        195                 200                 205
Lys Asp Arg Asn Glu Ala Arg Asp His Met Val Leu Leu Glu Phe Phe
    210                 215                 220
Ser Ala Cys Gly His Thr His Gly Met Asp Glu Leu Tyr Arg
225                 230                 235

<210> SEQ ID NO 7
<211> LENGTH: 717
<212> TYPE: DNA
<213> ORGANISM: Artificial sequence
<220> FEATURE:
<223> OTHER INFORMATION: Mut 235-1 protein derived from Aequorea
      macrodactyla GFPxm, nucleotide sequence with humanized codon
      usage

<400> SEQUENCE: 7
atgagcgggg gcgaggagct gttcgccggc atcgtgcccg tgctgatcga gctggacggc      60
gacgtgcacg gccacaagtt cagcgtgcgc ggcgagggcg agggcgacgc cgactacggc     120
aagctggaga tcaagttcat ctgcaccacc ggcaagctgc ccgtgccctg gcccaccctg     180
gtgaccacct tcagctacgg catccagtgc ttcgcccgct accccgagca catgaagatg     240
aacgacttct tcaagagcgc catgcccgag ggctacatcc aggagcgcac catcctcttc     300
caggacgacg gcaagtacaa gacccgcggc gaggtgaagt tcgagggcga caccctggtg     360
aaccgcatcg agctgaaggg caaggacttc aaggaggacg gcaacatcct gggccacaag     420
ctggagtaca gcttcaacag ccacaacgtg tacatcatgc ccgacaaggc caacaacggc     480
ctgaaggtga acttcaagat ccgccacaac atcgagggcg gcggcgtgca gctggccgac     540
cactaccaga ccaacgtgcc cctgggcgac ggccccgtgc tgatccccat caaccactac     600
ctgagcaccc agaccgccat cagcaaggac cgcaacgagg cccgcgacca catggtgctc     660
ctggagttct tcagcgcctg cggccacacc cacggcatgg acgagctgta caggtga        717

<210> SEQ ID NO 8
<211> LENGTH: 238
<212> TYPE: PRT

<213> ORGANISM: Artificial sequence
<220> FEATURE:
<223> OTHER INFORMATION: Mut 235-1 protein derived from Aequorea
      macrodactyla GFPxm

<400> SEQUENCE: 8

| Met | Ser | Gly | Gly | Glu | Glu | Leu | Phe | Ala | Gly | Ile | Val | Pro | Val | Leu | Ile |
| 1 | | | | 5 | | | | | 10 | | | | | 15 | |

| Glu | Leu | Asp | Gly | Asp | Val | His | Gly | His | Lys | Phe | Ser | Val | Arg | Gly | Glu |
| | | | 20 | | | | | 25 | | | | | 30 | | |

| Gly | Glu | Gly | Asp | Ala | Asp | Tyr | Gly | Lys | Leu | Glu | Ile | Lys | Phe | Ile | Cys |
| | | 35 | | | | | 40 | | | | | 45 | | | |

| Thr | Thr | Gly | Lys | Leu | Pro | Val | Pro | Trp | Pro | Thr | Leu | Val | Thr | Thr | Phe |
| 50 | | | | | 55 | | | | | 60 | | | | | |

| Ser | Tyr | Gly | Ile | Gln | Cys | Phe | Ala | Arg | Tyr | Pro | Glu | His | Met | Lys | Met |
| 65 | | | | 70 | | | | | 75 | | | | | 80 | |

| Asn | Asp | Phe | Phe | Lys | Ser | Ala | Met | Pro | Glu | Gly | Tyr | Ile | Gln | Glu | Arg |
| | | | | 85 | | | | | 90 | | | | | 95 | |

| Thr | Ile | Leu | Phe | Gln | Asp | Asp | Gly | Lys | Tyr | Lys | Thr | Arg | Gly | Glu | Val |
| | | | 100 | | | | | 105 | | | | | 110 | | |

| Lys | Phe | Glu | Gly | Asp | Thr | Leu | Val | Asn | Arg | Ile | Glu | Leu | Lys | Gly | Lys |
| | | 115 | | | | | 120 | | | | | 125 | | | |

| Asp | Phe | Lys | Glu | Asp | Gly | Asn | Ile | Leu | Gly | His | Lys | Leu | Glu | Tyr | Ser |
| 130 | | | | | 135 | | | | | 140 | | | | | |

| Phe | Asn | Ser | His | Asn | Val | Tyr | Ile | Met | Pro | Asp | Lys | Ala | Asn | Asn | Gly |
| 145 | | | | 150 | | | | | 155 | | | | | 160 | |

| Leu | Lys | Val | Asn | Phe | Lys | Ile | Arg | His | Asn | Ile | Glu | Gly | Gly | Gly | Val |
| | | | | 165 | | | | | 170 | | | | | 175 | |

| Gln | Leu | Ala | Asp | His | Tyr | Gln | Thr | Asn | Val | Pro | Leu | Gly | Asp | Gly | Pro |
| | | | 180 | | | | | 185 | | | | | 190 | | |

| Val | Leu | Ile | Pro | Ile | Asn | His | Tyr | Leu | Ser | Thr | Gln | Thr | Ala | Ile | Ser |
| | | | 195 | | | | | 200 | | | | | 205 | | |

| Lys | Asp | Arg | Asn | Glu | Ala | Arg | Asp | His | Met | Val | Leu | Leu | Glu | Phe | Phe |
| 210 | | | | | 215 | | | | | 220 | | | | | |

| Ser | Ala | Cys | Gly | His | Thr | His | Gly | Met | Asp | Glu | Leu | Tyr | Arg | | |
| 225 | | | | 230 | | | | | 235 | | | | | | |

<210> SEQ ID NO 9
<211> LENGTH: 717
<212> TYPE: DNA
<213> ORGANISM: Artificial sequence
<220> FEATURE:
<223> OTHER INFORMATION: Mut 235-2 protein derived from Aequorea
      macrodactyla GFPxm, nucleotide sequence with humanized codon
      usage

<400> SEQUENCE: 9

```
atgagcgggg gcgaggagct gttcaccggc atcgtgcccg tgctgatcga gctggacggc      60
gacgtgcacg gccacaagtt cagcgtgcgc ggcgagggcg agggcgacgc cgactacggc     120
aagctggaga tcaagttcat ctgcaccacc ggcaagctgc ccgtgccctg gaccaccctg     180
gtgaccacct tcagctacgg catccagtgc ttcgcccgct accccgagca catgaagatg     240
aacgacttct tcaagagcgc catgcccgag ggctacatcc aggagcgcac catcttcttc     300
caggacgacg gcaagtacaa gacccgcggc gaggtgaagt tcgagggcga caccctggtg     360
aaccgcatcg agctgaaggg catggacttc aaggaggacg caacatgct gggccacaag     420 ctggagtaca gcttcaacag ccacaacgtg tacatcatgc ccgacatggc caacaacggc     480
```

```
ctgaaggtga acttcaagat ccgccacaac atcgagggcg gcggcgtgca gctggccgac    540
cactaccaga ccaacgtgcc cctgggcgac ggccccgtgc tgatccccat caaccactac    600
ctgagcaccc agaccgccat cagcaaggac cgcaacgagg cccgcgacca catggtgctc    660
ctggagttct tcagcgcctg cggccacacc cacggcatgg acgagctgta caggtga      717
```

<210> SEQ ID NO 10
<211> LENGTH: 238
<212> TYPE: PRT
<213> ORGANISM: Artificial sequence
<220> FEATURE:
<223> OTHER INFORMATION: Mut 235-2 protein derived from Aequorea
      macrodactyla GFPxm

<400> SEQUENCE: 10

```
Met Ser Gly Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Thr Thr Leu Val Thr Thr Phe
    50                  55                  60

Ser Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Met Leu Gly His Lys Leu Glu Tyr Ser
    130                 135                 140

Phe Asn Ser His Asn Val Tyr Ile Met Pro Asp Met Ala Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Ala Ile Ser
        195                 200                 205

Lys Asp Arg Asn Glu Ala Arg Asp His Met Val Leu Leu Glu Phe Phe
    210                 215                 220

Ser Ala Cys Gly His Thr His Gly Met Asp Glu Leu Tyr Arg
225                 230                 235
```

<210> SEQ ID NO 11
<211> LENGTH: 717
<212> TYPE: DNA
<213> ORGANISM: Artificial sequence
<220> FEATURE:
<223> OTHER INFORMATION: Mut 235-4 protein derived from Aequorea
      macrodactyla GFPxm, nucleotide sequence with humanized codon
      usage

<400> SEQUENCE: 11

```
atgagcgggg gcgaggagct gttcaccggc atcgtgcccg tgctgatcga gctggacggc    60
```

```
gacgtgcacg gccacaagtt cagcgtgcgc ggcgagggcg agggcgacgc cgactacggc      120
aagctggaga tcaagttcat ctgcaccacc ggcaagctgc ccgtgccctg gcccaccctg      180
gtgaccacct tcagctacgg catccagtgc ttcgcccgct accccgagca tatgaagatg      240
aacgacttct tcaagagcgc catgcccgag ggctacatcc aggagcgcac catcttcttc      300
caggacgacg gcaagtacaa gacccgcggc gaggtgaagt tcgagggcga caccctggtg      360
aaccgcatcg agctgaaggg catggacttc aaggaggacg gcaacatcct gggccacaag      420
ctggagtaca gcttcaacag ccacaacgtg cacatcatgc ccgacaaggc caacaacggc      480
ctgaaggtga acttcaagat ccgccacaac atcgagggcg gcggcgtgca gctggccgac      540
cactaccaga ccaacgtgcc cctgggcgac ggccccgtgc tgatccccat caaccactac      600
ctgagcaccc agaccgccat cagcaaggac cgcaacgagg cccgcgacca catggtgctc      660
ctggagttct tcagcgcctg cggccacacc cacggcatgg acgagctgta caggtga         717
```

<210> SEQ ID NO 12
<211> LENGTH: 238
<212> TYPE: PRT
<213> ORGANISM: Artificial sequence
<220> FEATURE:
<223> OTHER INFORMATION: Mut 235-4 protein derived from Aequorea macrodactyla GFPxm

<400> SEQUENCE: 12

```
Met Ser Gly Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Phe
    50                  55                  60

Ser Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Ser
    130                 135                 140

Phe Asn Ser His Asn Val His Ile Met Pro Asp Lys Ala Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Ala Ile Ser
        195                 200                 205

Lys Asp Arg Asn Glu Ala Arg Asp His Met Val Leu Leu Glu Phe Phe
    210                 215                 220

Ser Ala Cys Gly His Thr His Gly Met Asp Glu Leu Tyr Arg
225                 230                 235
```

-continued

<210> SEQ ID NO 13
<211> LENGTH: 717
<212> TYPE: DNA
<213> ORGANISM: Artificial sequence
<220> FEATURE:
<223> OTHER INFORMATION: Mut-g9 protein derived from Aequorea
      macrodactyla GFPxm, nucleotide sequence with humanized codon
      usage

<400> SEQUENCE: 13

```
atgagcgggg gcgaggagct gttcgccggc atcgtgcccg tgctgatcga gctggacggc    60
gacgtgcacg gccacaagtt cagcgtgcgc ggcgagggcg agggcgacgc cgactacggc   120
aagctggaga tcaagttcat ctgcaccacc ggcaagctgc ccgtgccctg gcccaccctg   180
gtgaccacct tcagctacgg catccagtgc ttcgcccgct accccgagca catgaagatg   240
aacgacttct tcaagagcgc catgcccgag ggctacatcc aggagcgcac catcctcttc   300
caggacgacg gcaagtacaa gacccgcggc gaggtgaagt tcgagggcga cacccctggtg 360
aaccgcatcg agctgaaggg caaggacttc aaggaggacg gcaacatcct gggccacaag   420
ctggagtaca gcttcaacag ccacaacgtg tacatcatgc ccgacaaggc caacaacggc   480
ctggaggtga acttcaagat ccgccacaac atcgagggcg gcggcgtgca gctggccgac   540
cactaccaga ccaacgtgcc cctgggcgac ggccccgtgc tgatccccat caaccactac   600
ctgagcaccc agaccgccat cagcaaggac cgcaacgagg cccgcgacca catggtgctc   660
ctggagttct tcagcgcctg ctgccacacc cacggcatgg acgagctgta caggtga      717
```

<210> SEQ ID NO 14
<211> LENGTH: 238
<212> TYPE: PRT
<213> ORGANISM: Artificial sequence
<220> FEATURE:
<223> OTHER INFORMATION: Mut-g9 protein derived from Aequorea
      macrodactyla GFPxm

<400> SEQUENCE: 14

```
Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Phe
    50                  55                  60

Ser Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Leu Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
    130                 135                 140

Phe Asn Ser His Asn Val Tyr Ile Met Pro Asp Lys Ala Asn Asn Gly
145                 150                 155                 160

Leu Glu Val Asn Phe Lys Ile Arg His Asn Ile Glu Gly Gly Gly Val
                165                 170                 175
```

-continued

```
Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Ala Ile Ser
        195                 200                 205

Lys Asp Arg Asn Glu Ala Arg Asp His Met Val Leu Leu Glu Phe Phe
    210                 215                 220

Ser Ala Cys Cys His Thr His Gly Met Asp Glu Leu Tyr Arg
225                 230                 235
```

<210> SEQ ID NO 15
<211> LENGTH: 717
<212> TYPE: DNA
<213> ORGANISM: Artificial sequence
<220> FEATURE:
<223> OTHER INFORMATION: 235-4G6 protein derived from Aequorea macrodactyla GFPdnaxm, nucleotide sequence with humanized codon usage

<400> SEQUENCE: 15

```
atgagcgggg gcgaggacct gttcaccggc atcgtgcccg tgctgatcga gctggacggc    60
gacgtgcacg gccacaagtt cagcgtgcgc ggcgagggcg agggcgacgc cgactacggc   120
aagctggaga tcaagttcat ctgcaccacc ggcaagctgc ccgtgccctg gcccaccctg   180
gtgaccacct tcagctacgg catccagtgc ttcgcccgct accccgagca tatgaagatg   240
aacgacttct tcaagagcgc catgcccgag ggctacatcc aggagcgcac catcttcttc   300
caggacgacg gcaagtacaa gacccgcggc gaggtgaagt cgagggcga caccctggtg   360
aaccgcatcg agctgaaggg catggacttc aaggaggacg gcaacatcct gggccacaag   420
ctggagtaca gcttcaacag ccacaacgtg cacatcatgc ccgacaaggc caacaacggc   480
ctgaaggtga acttcaagat ccgccacaac atcgagggcg gcggcgtgca gctggccgac   540
cactaccaga ccaacgtgcc cctgggcgac ggccccgtgc tgatccccat caaccactac   600
ctgagcaccc agaccgccat cagcaaggac cgcaacgagg cccgcgacca tatggtgctc   660
ctggagttct tcagcgcctg cggccacacc cacggcatgg acgagctgta caggtga      717
```

<210> SEQ ID NO 16
<211> LENGTH: 238
<212> TYPE: PRT
<213> ORGANISM: Artificial sequence
<220> FEATURE:
<223> OTHER INFORMATION: 235-4G6 protein derived from Aequorea macrodactyla GFPxm

<400> SEQUENCE: 16

```
Met Ser Gly Gly Glu Asp Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Phe
    50                  55                  60

Ser Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110
```

```
Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Ser
    130                 135                 140

Phe Asn Ser His Asn Val His Ile Met Pro Asp Lys Ala Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Ala Ile Ser
        195                 200                 205

Lys Asp Arg Asn Glu Ala Arg Asp His Met Val Leu Leu Glu Phe Phe
    210                 215                 220

Ser Ala Cys Gly His Thr His Gly Met Asp Glu Leu Tyr Arg
225                 230                 235
```

<210> SEQ ID NO 17
<211> LENGTH: 717
<212> TYPE: DNA
<213> ORGANISM: Artificial sequence
<220> FEATURE:
<223> OTHER INFORMATION: tagGFP, nucleotide sequence with humanized codon usage

<400> SEQUENCE: 17

```
atgagcgggg gcgaggagct gttcgccggc atcgtgcccg tgctgatcga gctggacggc     60
gacgtgcacg gccacaagtt cagcgtgcgc ggcgagggcg agggcgacgc cgactacggc    120
aagctggaga tcaagttcat ctgcaccacc ggcaagctgc cgtgccctg gcccaccctg    180
gtgaccaccc tctgctacgg catccagtgc ttcgcccgct accccgagca catgaagatg    240
aacgacttct tcaagagcgc catgcccgag ggctacatcc aggagcgcac catcctcttc    300
caggacgacg gcaagtacaa gacccgcggc gaggtgaagt cgagggcga cacccctggtg   360
aaccgcatcg agctgaaggg caaggacttc aaggaggacg gcaacatcct gggccacaag    420
ctggagtaca gcttcaacag ccacaacgtg tacatcatgc cgacaaggc caacaacggc     480
ctggaggtga acttcaagac ccgccacaac atcgagggcg gcggcgtgca gctggccgac    540
cactaccaga ccaacgtgcc cctgggcgac ggccccgtgc tgatccccat caaccactac    600
ctgagcaccc agaccgccat cagcaaggac cgcaacgag cccgcgacca catggtgctc    660
ctggagtcct tcagcgcctg ctgccacacc cacggcatgg acgagctgta caggtga      717
```

<210> SEQ ID NO 18
<211> LENGTH: 238
<212> TYPE: PRT
<213> ORGANISM: Artificial sequence
<220> FEATURE:
<223> OTHER INFORMATION: tagGFP amino acid sequence

<400> SEQUENCE: 18

```
Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45
```

Thr Thr Gly Lys Leu Pro Val Pro Trp Pro Thr Leu Val Thr Thr Leu
50                  55                  60

Cys Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Leu Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
130                 135                 140

Phe Asn Ser His Asn Val Tyr Ile Met Pro Asp Lys Ala Asn Asn Gly
145                 150                 155                 160

Leu Glu Val Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Ala Ile Ser
        195                 200                 205

Lys Asp Arg Asn Glu Ala Arg Asp His Met Val Leu Leu Glu Ser Phe
210                 215                 220

Ser Ala Cys Cys His Thr His Gly Met Asp Glu Leu Tyr Arg
225                 230                 235

<210> SEQ ID NO 19
<211> LENGTH: 717
<212> TYPE: DNA
<213> ORGANISM: Artificial sequence
<220> FEATURE:
<223> OTHER INFORMATION: tagCFP, nucleotide sequence with humanized
      codon usage

<400> SEQUENCE: 19

```
atgagcgggg gcgaggagct gttcgctggc atcgtgcccg tgctgatcga gctggacggc      60
gacgtgcacg gccacaagtt cagcgtgcgc ggtgagggag agggcgacgc cgactacggc     120
aagctggaga tcaagttcat ctgcaccacc ggcaagctgc cgtgccctg cccaccctg       180
gtgaccaccc tcgcctgggg catccagtgc ttcgcccgct accccgagca catgaagatg     240
aacgacttct tcaagagcgc catgcccgag ggctacatcc aggagcgcac catccacttc     300
caggacgacg gcaagtacaa gacccgcggc gaggtgaagt tcgagggcga caccctggtg     360
aaccgcgtcg agctgaaggg cgagggcttc aaggaggacg gcaacatcct gggccacaag     420
ttggagtaca gcgccatcag cgacaacgtg tacatcatgc ccgacaaggc caacaacggc     480
ctggaggcga acttcaagat ccgccacaac atcgagggcg gcggcgtgca gctggccgac     540
cactaccaga ccaacgtgcc cctgggcgat ggccccgtgc tgatccccat caaccactac     600
ctgagctgcc agtccgccat cagcaaggac cgcaacgaag cccgcgacca catggtgctc     660
ctggagtcct tcagcgccta ctgccacacc cacggcatgg acgagctgta ccgctaa       717
```

<210> SEQ ID NO 20
<211> LENGTH: 238
<212> TYPE: PRT
<213> ORGANISM: Artificial sequence
<220> FEATURE:
<223> OTHER INFORMATION: tagCFP amino acid sequence -continued

<400> SEQUENCE: 20

```
Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
50                  55                  60

Ala Trp Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile His Phe Gln Asp Asp Gly Lys Tyr Lys Thr Arg Gly Glu Val
            100                 105                 110

Lys Phe Glu Gly Asp Thr Leu Val Asn Arg Val Glu Leu Lys Gly Glu
        115                 120                 125

Gly Phe Lys Glu Asp Gly Asn Ile Leu Gly His Lys Leu Glu Tyr Ser
130                 135                 140

Ala Ile Ser Asp Asn Val Tyr Ile Met Pro Asp Lys Ala Asn Asn Gly
145                 150                 155                 160

Leu Glu Ala Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Cys Gln Ser Ala Ile Ser
        195                 200                 205

Lys Asp Arg Asn Glu Ala Arg Asp His Met Val Leu Leu Glu Ser Phe
210                 215                 220

Ser Ala Tyr Cys His Thr His Gly Met Asp Glu Leu Tyr Arg
225                 230                 235
```

<210> SEQ ID NO 21
<211> LENGTH: 717
<212> TYPE: DNA
<213> ORGANISM: Artificial sequence
<220> FEATURE:
<223> OTHER INFORMATION: tagYFP1, nucleotide sequence with humanized codon usage

<400> SEQUENCE: 21

```
atgagcgggg gcgaggagct gttcgccggc atcgtgcccg tgctgatcga gctggacggc      60
gacgtgcacg gccacaagtt cagcgtgcgc ggcgagggcg agggcgacgc cgactacggc     120
aagctggaga tcaagttcat ctgcaccacc ggcaagctgc cgtgccctg cccacctg       180 gtgaccaccc tcacctacgg cgtacagtgc ttcgcccgct accccaagca catgaagatg     240
aacgacttct tcaagagcgc catgcccgag ggctacatcc aggagcgcac catcctcttc     300
caagacgacg gcaagtacaa gacccgcggc gaggtgaagt tcgagggcga cacccctggtg    360 aaccgcatcg agctgaaggg caaggacttc aaggaggacg gcaacatcct gggccacaag     420
ctggagtaca gcttcaacag ccacaacgtc tacatcaccc cgacaaggc caacaacggc      480 ctggaggtga acttcaagac ccgccacaac atcgagggcg gcggcgtgca gctggccgac     540
cactaccaga ccaacgtgcc cctgggcgac ggccccgtgc tgatccccat caaccactac     600
ctgagctacc agaccgccat cagcaaggac cgcaacgagg cccgcgacca catggtgctc     660
```
ctggagtccg tcagcgcctg cagccacacc cacggcatgg acgagctgta ccgctga 717

```
<210> SEQ ID NO 22
<211> LENGTH: 238
<212> TYPE: PRT
<213> ORGANISM: Artificial sequence
<220> FEATURE:
<223> OTHER INFORMATION: tagYFP1 amino acid sequence

<400> SEQUENCE: 22
```

Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ala Arg Tyr Pro Lys His Met Lys Met
65                  70                  75                  80

Asn Asp Phe Phe Lys Ser Ala Met Pro Glu Gly Tyr Ile Gln Glu Arg
                85                  90                  95

Thr Ile Leu Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
    130                 135                 140

Phe Asn Ser His Asn Val Tyr Ile Thr Pro Asp Lys Ala Asn Asn Gly
145                 150                 155                 160

Leu Glu Val Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Tyr Gln Thr Ala Ile Ser
        195                 200                 205

Lys Asp Arg Asn Glu Ala Arg Asp His Met Val Leu Leu Glu Ser Val
    210                 215                 220

Ser Ala Cys Ser His Thr His Gly Met Asp Glu Leu Tyr Arg
225                 230                 235

```
<210> SEQ ID NO 23
<211> LENGTH: 717
<212> TYPE: DNA
<213> ORGANISM: Artificial sequence
<220> FEATURE:
<223> OTHER INFORMATION: tagYFP2, nucleotide sequence with humanized
      codon usage

<400> SEQUENCE: 23
```
atgagcgggg gcgaggagct gttcgccggc atcgtgcccg tgctgatcga gctggacggc    60
gacgtgcacg gccacaagtt cagcgtgcgc ggcgagggcg agggcgacgc cgactacggc   120
aagctggaga tcaagttcat ctgcaccacc ggcaagctgc ccgtgccctg gcccaccctg   180
gtgaccaccc tcacctacgg cgtacagtgc ttcgcccgct accccaagca catgaagatg   240
aacgacttct tcaagagcgc catgcccgag ggctacatcc aggagcgcac catcctcttc   300

```
caagacgacg gcaagtacaa gacccgcggc gaggtgaagt tcgagggcga cccctggtg    360 aaccgcatcg agctgaaggg caaggacttc aaggaggacg gcaacatcct gggccacaag    420
ctggagtaca gcttcaacag ccacaacgtc tacatcaccc ccgacaaggc caacaacggc    480
ctggaggtga acttcaagac ccgccacaac atcgagggcg gcggcgtgca gctggccgac    540
cactaccaga ccaacgtgcc cctgggcgac ggccccgtgc tgatccccat caaccactac    600
ctgagctacc agaccgacat cagcaaggac cgcaacgagg cccgcgacca catggtgctc    660
ctggagtccg tcagcgcctg cagccacacc cacggcatgg acgagctgta ccgctga      717
```

<210> SEQ ID NO 24
<211> LENGTH: 238
<212> TYPE: PRT
<213> ORGANISM: Artificial sequence
<220> FEATURE:
<223> OTHER INFORMATION: tagYFP2 amino acid sequence

<400> SEQUENCE: 24

```
Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
                20                  25                  30

Gly Glu Gly Asp Ala Asp Tyr Gly Lys Leu Glu Ile Lys Phe Ile Cys
            35                  40                  45

Thr Thr Gly Lys Leu Pro Val Pro Trp Pro Thr Leu Val Thr Thr Leu
        50                  55                  60

Thr Tyr Gly Val Gln Cys Phe Ala Arg Tyr Pro Lys His Met Lys Met
65                  70                  75                  80

Asn Asp Phe Phe Lys Ser Ala Met Pro Glu Gly Tyr Ile Gln Glu Arg
                85                  90                  95

Thr Ile Leu Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
    130                 135                 140

Phe Asn Ser His Asn Val Tyr Ile Thr Pro Asp Lys Ala Asn Asn Gly
145                 150                 155                 160

Leu Glu Val Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Tyr Gln Thr Asp Ile Ser
        195                 200                 205

Lys Asp Arg Asn Glu Ala Arg Asp His Met Val Leu Leu Glu Ser Val
    210                 215                 220

Ser Ala Cys Ser His Thr His Gly Met Asp Glu Leu Tyr Arg
225                 230                 235
```